(12) United States Patent
Chase et al.

(10) Patent No.: US 10,492,974 B2
(45) Date of Patent: Dec. 3, 2019

(54) COMPRESSION GARMENT SYSTEM WITH TIGHTENING APPARATUS

(71) Applicant: TACTILE SYSTEMS TECHNOLOGY, INC., Minneapolis, MN (US)

(72) Inventors: Daniel G. Chase, Menomonie, WI (US); Mark R. Riley, St. Paul, MN (US); Kristian Dior Gamble, Minneapolis, MN (US); Nicholas J. Haupt, St. Paul, MN (US)

(73) Assignee: Tactile Systems Technology, Inc., Minneapolis, MN (US)

( * ) Notice: Subject to any disclaimer, the term of this patent is extended or adjusted under 35 U.S.C. 154(b) by 269 days.

(21) Appl. No.: 15/319,179

(22) PCT Filed: Jun. 22, 2015

(86) PCT No.: PCT/US2015/036951
§ 371 (c)(1),
(2) Date: Dec. 15, 2016

(87) PCT Pub. No.: WO2015/200203
PCT Pub. Date: Dec. 30, 2015

(65) Prior Publication Data
US 2017/0128306 A1    May 11, 2017

Related U.S. Application Data

(60) Provisional application No. 62/015,897, filed on Jun. 23, 2014.

(51) Int. Cl.
*A61H 1/00* (2006.01)
*A61H 9/00* (2006.01)

(52) U.S. Cl.
CPC ........... *A61H 1/008* (2013.01); *A61H 9/0078* (2013.01); *A61H 2201/0192* (2013.01);
(Continued)

(58) Field of Classification Search
CPC ........ A61H 1/008; A61H 9/0078–0092; A61F 13/04; A61F 13/041; A61F 13/06; A61F 13/062
See application file for complete search history.

(56) References Cited

U.S. PATENT DOCUMENTS 1,795,893 A     3/1931 Rosett
3,659,593 A *   5/1972 Vail ..................... A61H 9/0078
                                                128/DIG. 15

(Continued)

FOREIGN PATENT DOCUMENTS

EP      2 226 044 A2    9/2010
EP      2 462 905 B1    11/2013

(Continued)

OTHER PUBLICATIONS

U.S. Appl. No. 29/576,157, filed Aug. 31, 2016, Chase et al.
(Continued)

*Primary Examiner* — Valerie L Woodward
(74) *Attorney, Agent, or Firm* — Mueting, Raasch & Gebhardt, P.A.

(57) ABSTRACT

Compression systems and methods for tightening a garment and/or applying a pressure through the garment may include a garment, a lacing system, and a tightening apparatus. The compression system may be used for tightening the garment about a portion of a body and/or applying pressure to a portion of the body by pressure applying regions of the garment. The lacing system may include lacing guide and at least one lace guided by the lacing guide members. The tightening apparatus may be coupled to the at least one lace (Continued)

and may be configured to apply tension on the at least one lace to tighten the garment about the portion of the body.

21 Claims, 12 Drawing Sheets

(52) U.S. Cl.
CPC ...... *A61H 2201/50* (2013.01); *A61H 2205/10* (2013.01); *A61H 2205/106* (2013.01); *A61H 2205/108* (2013.01); *A61H 2205/12* (2013.01); *A61H 2230/00* (2013.01)

(56) References Cited

U.S. PATENT DOCUMENTS

| | | | |
|---|---|---|---|
| 5,188,587 A | 2/1993 | McGuire et al. | |
| 5,997,465 A | 12/1999 | Savage et al. | |
| 6,179,796 B1 | 1/2001 | Waldridge | |
| 6,338,723 B1 | 1/2002 | Carpenter et al. | |
| 6,436,064 B1 | 8/2002 | Kloecker | |
| 6,645,165 B2 | 11/2003 | Waldridge et al. | |
| 6,860,862 B2 | 3/2005 | Waldridge et al. | |
| 6,966,884 B2 | 11/2005 | Waldridge et al. | |
| 7,044,924 B1* | 5/2006 | Roth ............... | A61H 9/0078 128/DIG. 20 |
| 7,591,050 B2 | 9/2009 | Hammerslag | |
| 7,631,382 B2 | 12/2009 | Dibenedetto et al. | |
| 7,857,777 B2* | 12/2010 | Larson ............. | A61B 17/1325 602/13 |
| 7,947,003 B2 | 5/2011 | Bonnefin et al. | |
| 8,046,937 B2 | 11/2011 | Beers et al. | |
| 8,096,964 B1 | 1/2012 | Bruehwiler et al. | |
| 8,381,362 B2 | 2/2013 | Hammerslag et al. | |
| 8,764,689 B2 | 7/2014 | Toth | |
| 9,027,408 B2 | 5/2015 | Toth et al. | |
| 9,320,307 B2 | 4/2016 | Berns et al. | |
| 2003/0032905 A1 | 2/2003 | Waldridge et al. | |
| 2005/0126578 A1* | 6/2005 | Garrison ............ | A61H 9/0078 128/874 |
| 2006/0000478 A1 | 1/2006 | Taylor | |
| 2006/0156517 A1 | 7/2006 | Hammerslag et al. | |
| 2006/0200057 A1 | 9/2006 | Sterling | |
| 2007/0169378 A1 | 7/2007 | Sodeberg et al. | |
| 2009/0254014 A1 | 10/2009 | Son | |
| 2010/0228171 A1 | 9/2010 | Waldridge | |
| 2011/0009793 A1 | 1/2011 | Lucero et al. | |
| 2011/0087142 A1 | 4/2011 | Ravikumar et al. | |
| 2011/0257463 A1 | 10/2011 | Nour et al. | |
| 2012/0004587 A1* | 1/2012 | Nickel ............... | A61F 5/0118 602/21 |
| 2012/0150086 A1* | 6/2012 | Cohen ............... | A61F 5/0104 602/27 |
| 2012/0179084 A1 | 7/2012 | Lipshaw et al. | |
| 2012/0238924 A1* | 9/2012 | Avni ................. | A61H 9/0092 601/46 |
| 2013/0012856 A1 | 1/2013 | Hammerslag et al. | |
| 2013/0269219 A1 | 10/2013 | Burns et al. | |
| 2013/0345612 A1* | 12/2013 | Bannister ........... | A61B 5/1116 602/19 |
| 2014/0094728 A1* | 4/2014 | Soderberg .......... | A61F 5/028 602/6 |
| 2014/0123449 A1 | 5/2014 | Soderberg et al. | |
| 2014/0276274 A1* | 9/2014 | Clare ................ | A61H 1/008 601/84 |
| 2015/0157484 A1 | 6/2015 | Ex-Lubeskie et al. | |

FOREIGN PATENT DOCUMENTS

| | | |
|---|---|---|
| FR | 2 624 003 A1 | 11/1988 |
| FR | 2 939 642 A1 | 6/2010 |
| GB | 699152 | 10/1953 |
| WO | WO 03/041621 A1 | 5/2003 |
| WO | WO 2008/033963 A2 | 3/2008 |
| WO | WO 2014/159706 A2 | 10/2014 |

OTHER PUBLICATIONS

U.S. Appl. No. 29/576,182, filed Aug. 31, 2016, Chase et al.
U.S. Appl. No. 15/284,858, filed Oct. 4, 2016, Wennen et al.
U.S. Appl. No. 15/284,870, filed Oct. 4, 2016, Wennen et al.
U.S. Appl. No. 15/284,888, filed Oct. 4, 2016 Wennen et al.
U.S. Appl. No. 15/286,378, filed Oct. 5, 2016, Chase et al.
U.S. Appl. No. 15/411,003, filed Jan. 20, 2017, Wennen et al.
U.S. Appl. No. 15/411,059, filed Jan. 20, 2017, Chase et al.
U.S. Appl. No. 29/595,538, filed Feb. 28, 2017, Chase et al.
U.S. Appl. No. 29/596,757, filed Mar. 10, 2017, Wennen et al.
[US] International Patent Application No. PCT/2015/36951, filed Jun. 22, 2015; [International Search Report / Written Opinion] dated Nov. 13, 2015; 12 pages.
[US] International Patent Application No. PCT/US2015/36951, filed Jun, 22, 2015; [International Preliminary Report on Patentability] dated Jan. 5, 2017; 9 pages.
European Patent Application No. 15811233.4, filed Dec. 20, 2016; Extended European Search Report dated Oct. 19, 2017; 8 pages.

* cited by examiner

COMPRESSION GARMENT SYSTEM WITH TIGHTENING APPARATUS

CROSS-REFERENCE

This application is the § 371 U.S. National Stage of International Application No. PCT/US2015/36951, filed Jun. 22, 2015, which claims the benefit under 35 U.S.C. 119(e) of U.S. Provisional Application No. 62/015,897, filed Jun. 23, 2014, which are all incorporated herein by reference in their entireties.

FIELD OF THE DISCLOSURE

The present disclosure relates generally to use of tightening apparatus for compression garment systems and methods (e.g., lacing systems for use as donning apparatus, such as for closure, tightening, adjusting, etc., and/or lacing systems for use as compression apparatus).

BACKGROUND

Various types of compression garments are available, for example, such as for treatment of lymphedema, edema, wound healing, etc. For example, garments including inflatable cells to provide therapy to patients may be positioned about any body portion of a person or animal, such as a limb or limbs. Such cells may be inflatable to one or more different pressures in a variety of sequences to provide the therapy to the patient. In other words, such compression garments may be placed around at least a portion of an individual's body for use in applying pressure to the body at an affected extremity (e.g., arm, leg, torso, waist, a shoulder, hip, etc.). These compression garments may be donned (e.g., put on) and doffed (e.g., taken off) by patients themselves or with help from others. These actions by the patient may require flexibility and dexterity to correctly adjust and secure the compression garment into place. In patients that are older, donning and doffing the compression garment may be more complicated due to arthritis in the hands, fingers and other joints or other possible ailments.

SUMMARY

An exemplary compression system described herein may include a garment, a lacing system, a tightening apparatus, and a controller. The garment may be configured to wrap around at least a portion of a body. The garment may include a plurality of pressure applying regions (e.g., each pressure applying region of the plurality of pressure applying regions may be configured to apply pressure to the portion of the body). The lacing system may include a plurality of spaced apart lacing guide members (e.g., each lacing guide member may be positioned at a location on the garment) and at least one lace guided by the plurality of lacing guide members. The tightening apparatus may be coupled to the at least one lace and configured to apply tension on the at least one lace and thereby move at least one portion of the garment relative to another portion of the garment to tighten the garment about the portion of the body. The controller may be configured to control the pressure applied to the portion of the body by each of the pressure applying regions of the garment.

In one or more embodiments, the plurality of pressure applying regions may be configured to apply pressure and thereby move the garment closer and towards the portion of the body. In one or more embodiments, the compression system may also include at least one pressure sensor configured to measure pressure applied to the portion of the body by the garment and the controller may be configured to control the pressure applied to the portion of the body based on the measured pressure. In one or more embodiments, the plurality of pressure applying regions may include a plurality of compartments configured to receive a fluid. In one or more embodiments, the plurality of pressure applying regions may include a plurality of actuated elements configured to apply pressure to the portion of the body. In one or more embodiments, the tightening apparatus may include at least one tightening device configured to apply tension on the at least one lace and thereby move at least one portion of the garment relative to another to tighten the garment about the portion of the body and the tightening apparatus may be configured to apply further tension on the at least one lace after the at least one tightening device tightens the garment about, the portion of the body.

An exemplary method of compression therapy described herein may include applying a garment to at least a portion of a body. The garment may include a plurality of pressure applying regions and a lacing system including at least one lace that is guided by a plurality of spaced apart lacing guide members positioned on the garment. The method may also include tightening the at least one lace using a tightening apparatus. The tightening apparatus may be configured to apply tension on the at least one lace and thereby move one portion of the garment relative to another. The method may also include controlling pressure applied to the portion of the body at each of the pressure applying regions.

In one or more embodiments, the method may further include providing one or more compression devices. Each compression device of the one or more compression devices may include one or more tightening devices and controlling pressure applied to the portion of the body at each of the pressure applying regions may include controlling each of the one or more tightening devices operable in a lacing system to apply pressure to a portion of the body corresponding to a pressure applying region. In one or more embodiments, the tightening apparatus may include the one or more tightening devices. In one or more embodiments, the controlling pressure applied to the portion of the body at each of the pressure applying regions may include a first tightening device of the one or more tightening devices controllable to apply tension on at least one lace after a second tightening device of the one or more tightening devices applies tension on at least one lace.

In one or more embodiments, the method may further include providing one or more compression devices. Each compression device of the one or more compression devices may include one or more compartments and controlling pressure applied to the portion of the body at each of the pressure applying regions may include controlling fluid flow into the one or more compartments of each of the one or more compression devices to apply pressure to a portion of the body corresponding to a pressure applying region. In one or more embodiments, the method may further include loosening the at least one lace using the tightening apparatus.

An exemplary compression system described herein may include a garment, a lacing system, a tightening apparatus, and a controller. The garment may be configured to wrap around at least a portion of a body. The lacing system may include a plurality of lacing guide members (e.g., each lacing guide member may be positioned at a location of the garment) and at least one lace guided by the plurality of lacing members. The tightening apparatus may include a plurality of tightening devices corresponding to a plurality of regions of the garment and coupled to the at least one lace. The tightening apparatus may be configured to apply tension on the at least one lace and thereby move at least one portion of the garment relative to another portion of the garment to tighten the garment about the portion of the body. The plurality of tightening devices may be configured to apply a controlled pressure to a region of the portion of the body corresponding to the plurality of regions of the garment. The controller may be configured to control the pressure applied to the portion of the body by each of the plurality of regions of the garment.

In one or more embodiments, at least two of the plurality of tightening devices may be controllable by a controller to simultaneously apply the controlled pressure to the region of the portion of the body corresponding to the plurality of regions of the garment. In one or more embodiments, at least two of the plurality of tightening devices may be controllable by a controller to apply the controlled pressure to the region of the portion of the body corresponding to the plurality of regions of the garment in succession. In one or more embodiments, the system may further include a secondary pressure applying apparatus in addition to the tightening apparatus. The secondary pressure applying apparatus may be controllable by a controller to apply pressure to different regions of the portion of the body. In one or more embodiments the secondary pressure applying apparatus may include a plurality of compartments configured to receive a fluid. In one or more embodiments, the secondary pressure applying apparatus may include a plurality of actuated elements configured to apply pressure to the portion of the body.

An exemplary compression system described herein may include a garment, a lacing system, and a tightening apparatus. The garment may be configured to wrap around at least a portion of a body. The garment may include a plurality of compartments distributed along a length of the garment configured to receive a fluid, the plurality of compartments may form of one or more layers and a plurality of welds may be used to couple the one or more layers to define the plurality of compartments. The lacing system may include a plurality of spaced apart lacing guide members with each lacing guide member located adjacent one of the plurality of welds and at least one lace guided by the plurality of lacing guide members. The tightening apparatus may be coupled to the at least one lace. The tightening apparatus may be configured to apply tension on the at least one lace and thereby move at least one portion of the garment relative to another portion of the garment.

In one or more embodiments, the garment may further include at least one elongated rigid member that crosses at least two adjacent compartments. The at least one elongate rigid member may be more rigid than the one or more layers. In one or more embodiments, the garment may further include two or more elongated rigid members and at least one elastic bridge that may couple two elongated rigid members of the two or more elongated rigid members.

In one or more embodiments, each of the lacing guide members may include a guide member length that permits the at least one lace to move fluidly in the lacing guide member. In one or more embodiments, at least one weld of the plurality of welds extends along a weld axis. The at least one weld may include a weld width along the weld axis and the guide member length of at least one lacing guide member may be less than the weld width of the at least one weld. In one or more embodiments, at least one weld of the plurality of welds may include an elongate weld portion that extends along a weld axis and a cross weld portion extending a cross weld axis across the elongate weld portion. The elongate weld portion may include a weld width perpendicular to the weld axis. The cross weld axis of the cross weld portion extending across the elongate weld portion may be greater than the weld width of the at least one elongate weld portion and the guide member length of at least one lacing guide member may be less than the cross weld axis of the cross weld portion.

In one or more embodiments, the tightening apparatus may include a plurality of tightening devices configured to operate in a controlled manner relative to each other. In one or more embodiments, the plurality of tightening devices may be configured to operate in a sequence and each of the plurality of tightening devices may be configured to tighten to an independent torque.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
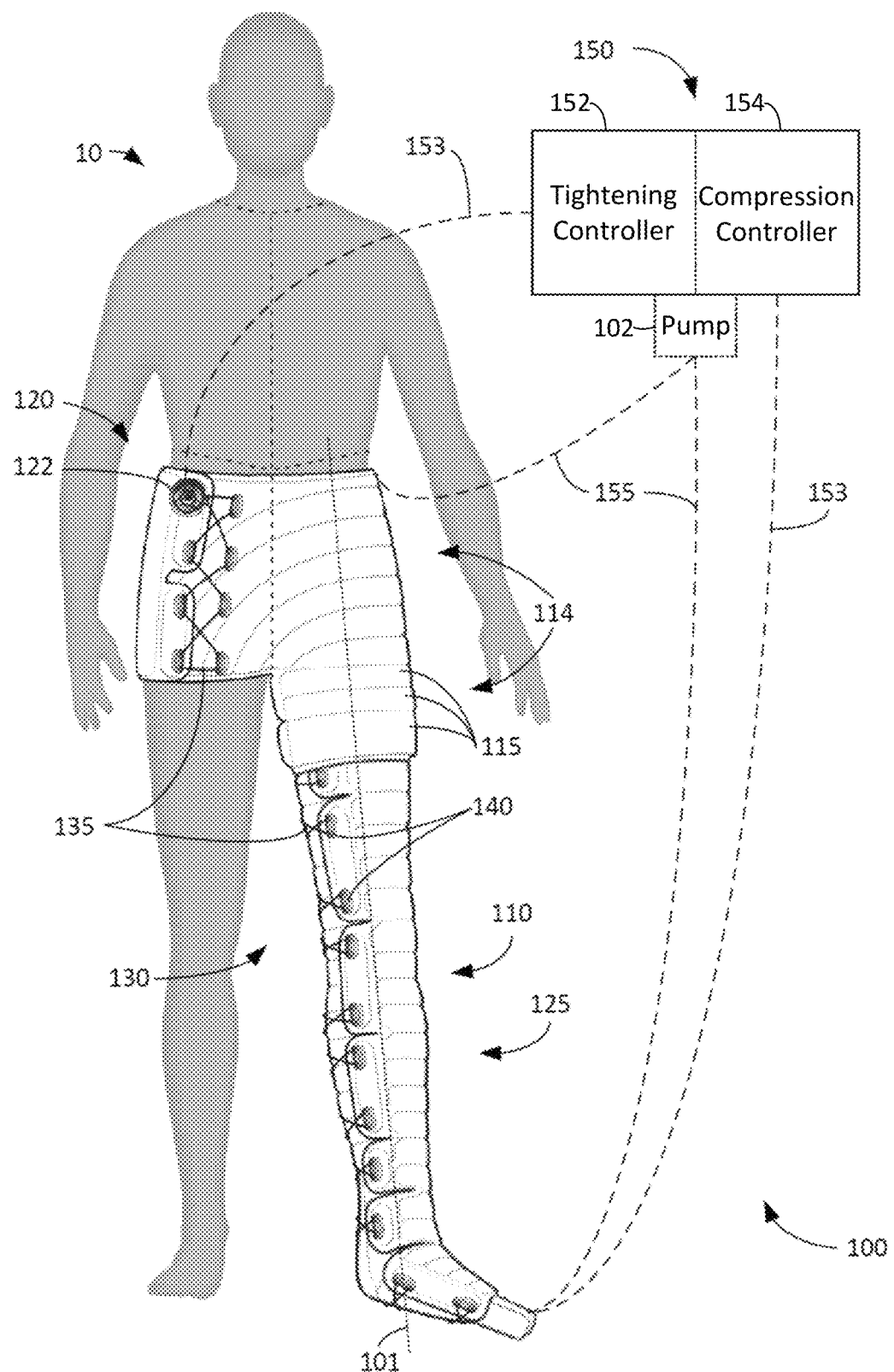
FIG. 1 is an exemplary compression system located on a body.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary apparatus, systems, structures, and methods shall be described with reference to FIGS. 1-12. It will be apparent to one skilled in the art that elements from one embodiment may be used in combination with elements of the other embodiments, and that the possible embodiments of such apparatus and systems using combinations of features set forth herein is not limited to the specific embodiments shown in the Figures and/or described herein. Further, it will be recognized that the embodiments described herein may include many elements that are not necessarily shown to scale. Still further, it will be recognized that the size and shape of various elements herein may be modified but still fall within the scope of the present disclosure, although certain one or more shapes and/or sizes, or types of elements, may be advantageous over others.

The present disclosure relates generally to compression garment systems that include donning apparatus (e.g., closure systems, tightening apparatus, garments, etc.), compression garment systems that include apparatus for controlling pressure applied to a body (e.g., person, animal, etc.) wearing a compression garment (e.g., with or without cells capable of being inflated with a fluid, such as air or gas) and methods using such systems (e.g., methods for controlling the closure systems, providing compression, etc.).

Compression garment systems (e.g., such as the Tactile Flexitouch product available from Tactile Systems, Inc., such as described in U.S. Pat. No. 6,179,796 entitled "Lymphedema treatment system" and U.S. Pat. No. 6,645,165 entitled "Lymphedema treatment system," which are herein incorporated by reference and which may be modified with features described herein), may be used for various reasons including therapy for people with lymphedema, animals requiring therapy, etc. as used herein, the term body refers to not only humans but any other animal species that may benefit from the concepts and features described herein. These compression garments may be placed around at least a portion of an individual's body and apply pressure to the body at an affected extremity (e.g., arm, leg, torso, waist, a shoulder, hip, etc.). The compression garments may be donned (e.g., put on) and doffed (e.g., taken off) by patients themselves or with help from others.

Some embodiments described herein may include a compression system having a garment configured to wrap around at least a portion of a body (e.g., human body, arm, leg, torso, waist, a shoulder, hip, head, neck, etc.). The garment may include a plurality of compartments (e.g., cells) distributed along a length of the garment configured to receive a fluid (e.g., air). The plurality of compartments may be formed of one or more layers. The garment may also include a plurality of welds used to couple the one or more layers to define the plurality of compartments. Such a compression system also may include a lacing system (e.g., at least one lace).

The lacing system may include a plurality of spaced apart lacing guide members (e.g., tubes, channels, open channels, hooks, loops, pulleys, etc.). Each lacing guide member may be located on a portion of the garment (e.g., adjacent one of the plurality of welds such as those used to create inflatable compartments, on an outer layer of the garment, adjacent an edge of the garment, etc.). In one or more embodiments, each lacing guide member may be located on, e.g., one of the plurality of welds, one of the layers of the garment. The lacing system may also include at least one lace (e.g., wire, cable, thread, etc.) guided by the plurality of lacing guide members and a tightening apparatus coupled to the at least one lace. The tightening apparatus may be configured to apply tension on the at least one lace and thereby move at least one portion of the garment relative to another portion of the garment to tighten the garment around the portion of the body.

Figure 2:
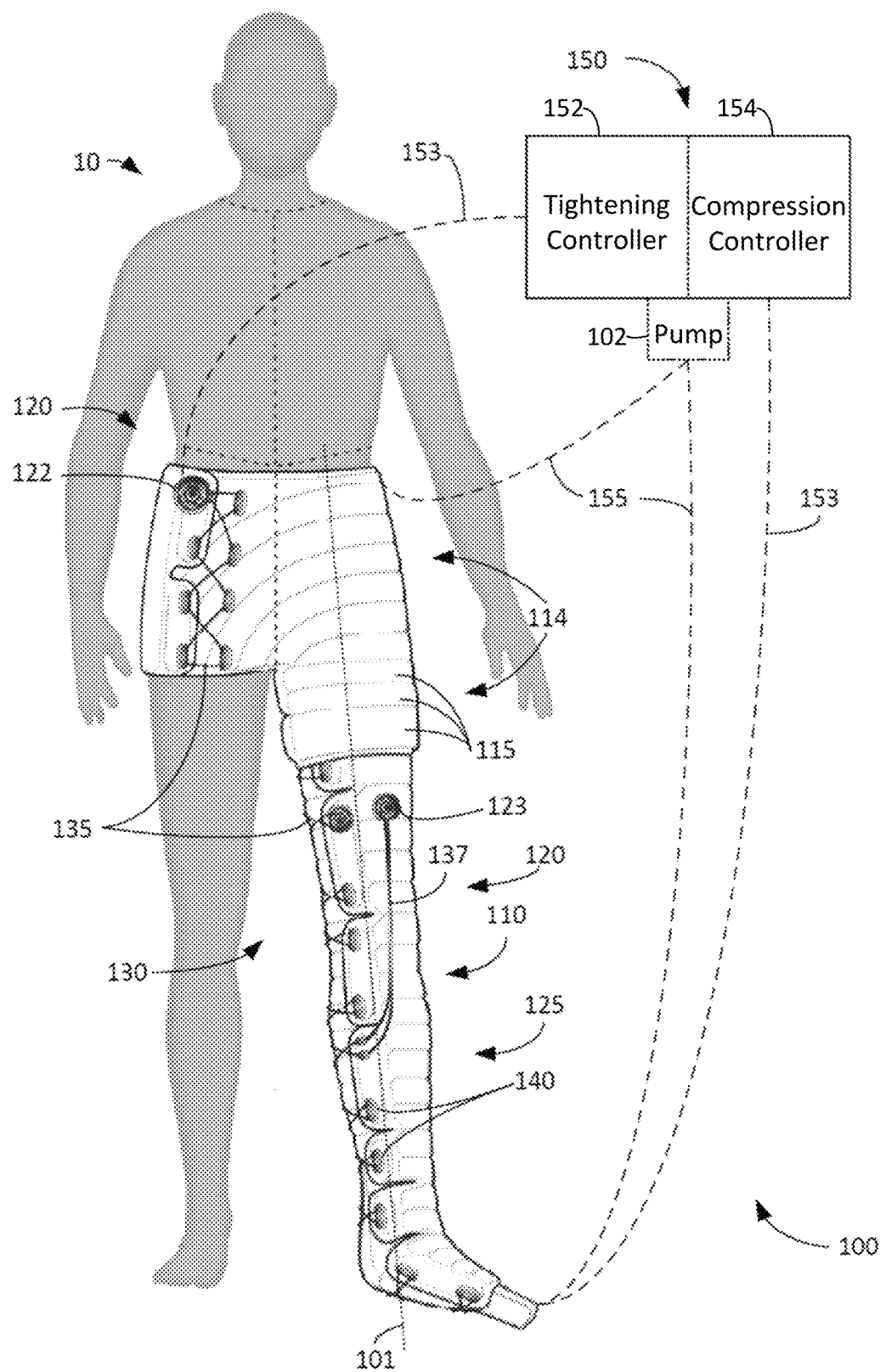
FIG. 2 is another exemplary compression system located on a body.
Figure 3:
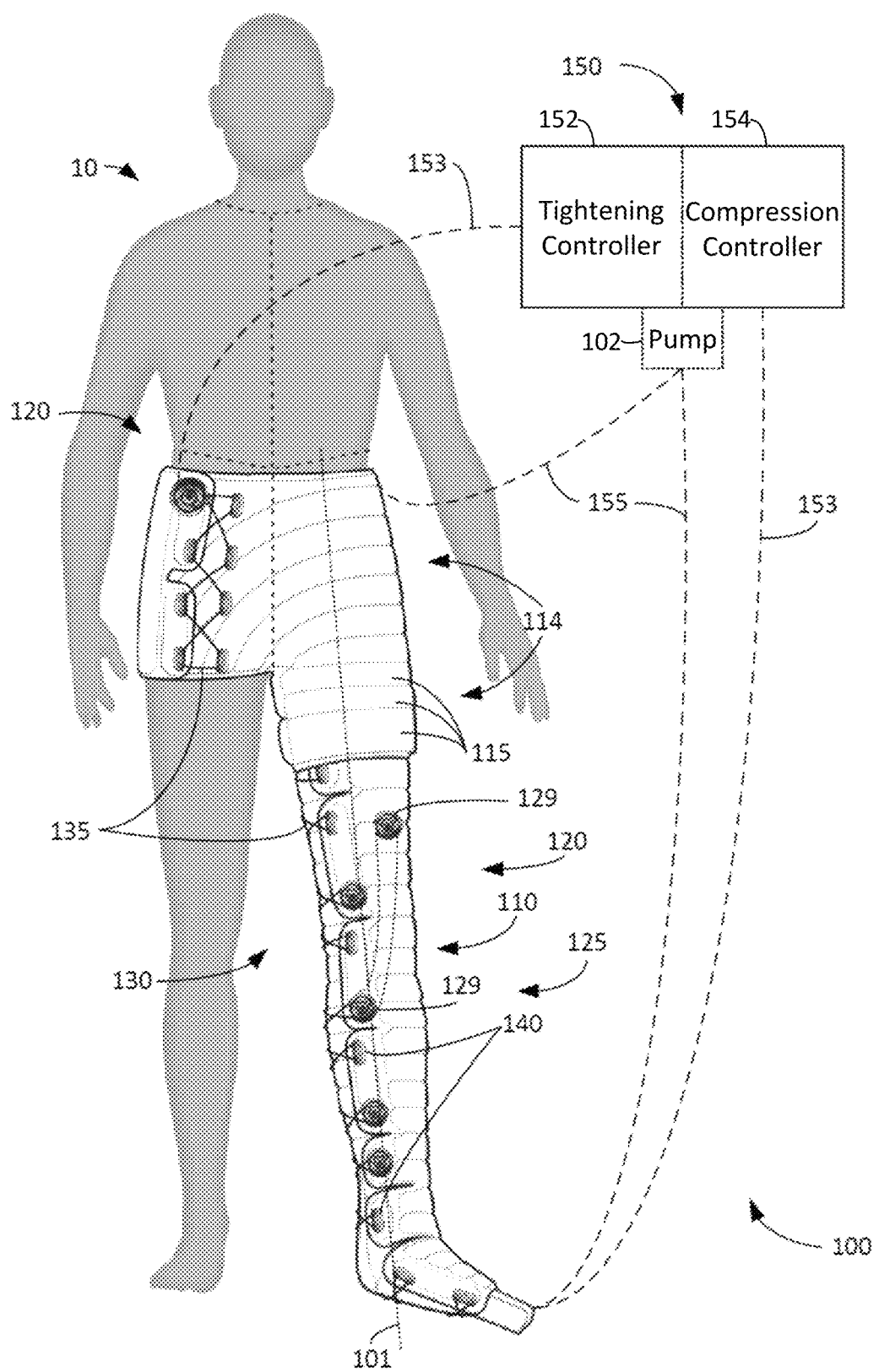
FIG. 3 is yet another exemplary compression system located on a body.

Exemplary compression systems 100 including a garment 110 (e.g., compression garment) configured to wrap around at least a portion of a body 10 (e.g., a human body) are shown in FIGS. 1-3. For simplicity purposes, the same numbers are used to reference features which are similar in the compression systems shown in such FIGS. 1-3 with different numbers being used to identify different features (e.g., even though any one or more of such different features may be used in combination in a compression garment). The garment 110 may be positioned relative to the body 10 in a variety of different ways. For example, a portion of the garment 110 may be positioned around a trunk of the body from the top of the thigh to the waist, around the thigh, from the knee to the top of the thigh, around the calf, from the ankle to the knee, or around the foot, from the toes to the ankle. The garment 110 may also cover the full leg to the trunk, all the way from the toes to the top of the waist with one continuous piece of fabric. It will be recognized that similar garments may be provided with features as described herein to cover other portions of the body. For example, garments may cover, for example, the shoulder, the torso, any portion of the arm, or any other portion of the body 10.

As shown in FIGS. 1-3, the garment 110 is located around the trunk of the body 10 and along the length of one leg of the body 10 to the foot. In some embodiments, the garment 110 may run along a length of an axis 101 formed by a body extremity (e.g., the leg as shown in FIGS. 1-3) or another portion of the body 10. The length of the garment 110 may be the distance along the axis 101 and the width of the garment 110 may be the distance circumferentially around the body portion of which the garment 110 is located. One or more garments that may be modified with features described herein may be similar to and include one or more features found in U.S. Pat. No. 6,860,862 entitled "Lymphedema Treatment System" and U.S. Pat. No. 6,966,884 entitled "Lymphedema Treatment System", which are herein incorporated by reference.

The garment 110 may include a plurality of pressure applying regions 114 configured or controllable to apply pressure to the portion of the body 10 as part of a compression device 125 of the compression system 100. The plurality of pressure applying regions 114 may be configured to apply pressure and move the garment 110 closer and towards the portion of the body 10. The plurality of pressure applying regions 114 may be any suitable arrangement of regions by which the compression system 100 distributes pressure along the body 10. For example, garment 110 may have a plurality of pressure applying regions 114 (e.g., lacing system regions, air chambers or cells, pneumatic pressure applying regions, actuatable elements applying pressure to regions, hydraulic pressure applying regions, etc.), with each region 114 configured to apply pressure to the portion of the body 10 (e.g., a different portion of the body).

Figure 6:
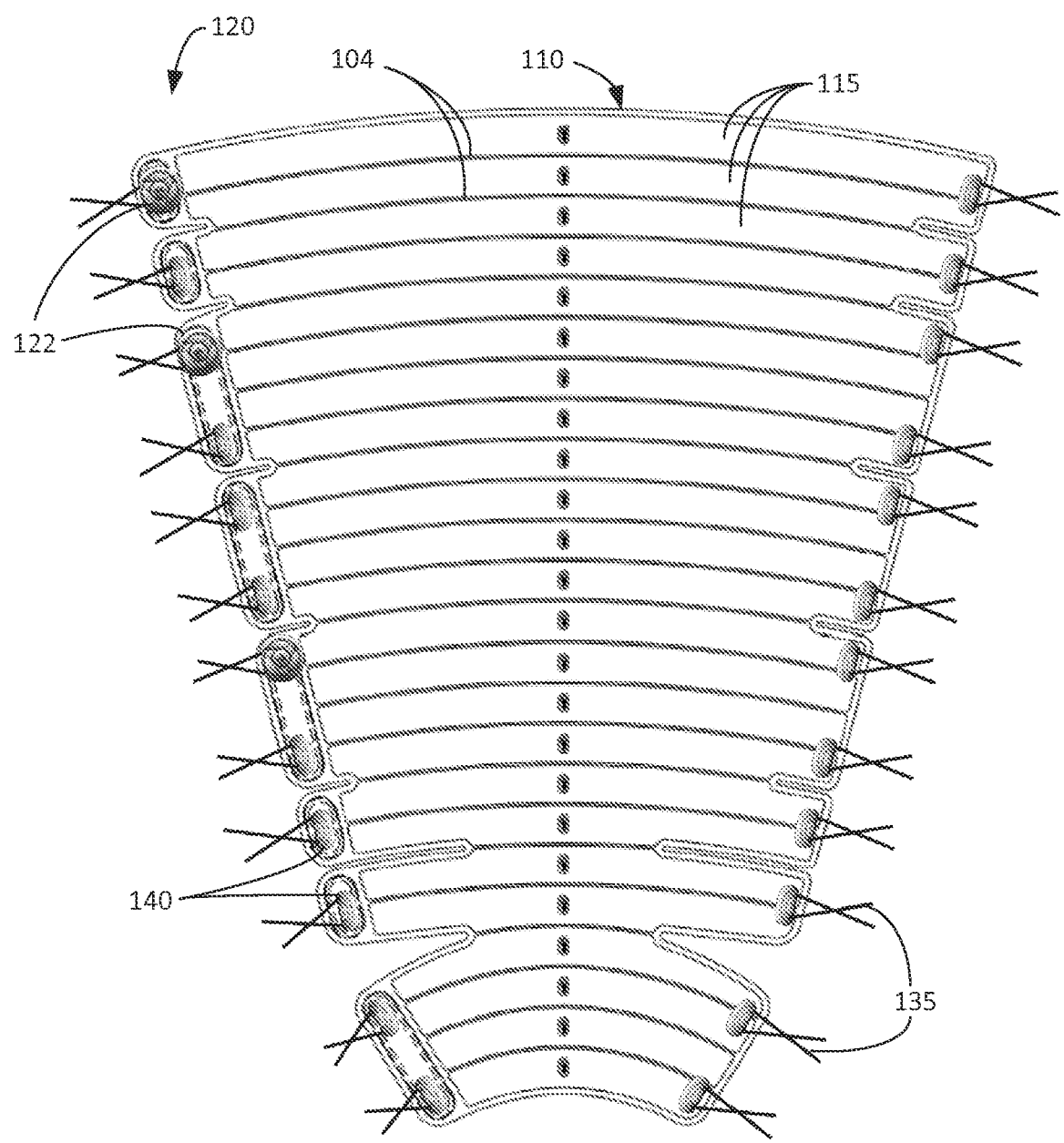
FIG. 6 is an exemplary garment including a plurality of compartments (e.g., inflatable cells) that may be used with one of the exemplary compression systems shown in FIGS. 1-3.

The plurality of pressure applying regions 114 may be located at various locations along the body 10 that correlate to specific regions that may be treated by the compression system 100. For example, the plurality of pressure applying regions 114 may be distributed based on portions of the body such as, the trunk, the leg, the thigh, the knee, the calf, the foot, etc. In one or more embodiments, the plurality of pressure applying regions 114 may be distributed based on compartments 115 located within the garment 110. For example, each compartment 115 may correspond to a pressure applying region 114, or multiple compartments 115 may correspond to a pressure applying region 114. In one or more embodiments, the compartments 115 may be separated by welds 104 (as shown in FIG. 6) to, e.g., isolate each compartment 115 from another compartment 115.

The system 100 may also include a lacing system 130. The lacing system 130 may be configured to assist in the donning and doffing of the garment 110 by tightening and loosening the garment 110 relative to the body 10 to, e.g., secure the garment 110 into place. In one or more embodiments, the lacing system 130 may also be configured or controlled to apply pressure to the pressure applying regions 114. The lacing system 130 may include a plurality of lacing guide members 140 that may be, e.g., spaced apart. Each lacing guide member 140 may be positioned at a location on the garment 110 (e.g., on a compartment 115, on a weld 104, between welds 104, overlapping a weld 104, etc.). In one or more embodiments, the lacing guide members 140 may be placed along one or both opposing edges of the garment 110 or spaced across a portion of the garment. 110 (e.g., spaced across a portion or the entire width of the garment or across a portion or the entire length of the garment). The lacing guide members 140 may be distributed on the garment 110 at a distance apart that would allow the garment 110 to tighten around the portion of the body 10 when the lacing guide members 140 move relative to one another.

The lacing system 130 may also include at least one lace 135 that may be guided by the plurality of lacing guide members 140. The at least one lace 135 may be used to tighten (or loosen) the garment 110 against or relative to the body 10 during, e.g., the donning (or doffing) process, compression at one or more pressure applying regions, etc. The at least one lace 135 may include a plurality of laces 135 or one continuous lace 135 positioned along the garment 110. The at least one lace 135 may include any material to provide sufficient durability and strength to allow tightening of a portion of the garment relative to the body 10, e.g., a leg. In other words, the at least one lace 135 may withstand forces applied on the at least one lace 135 to tighten the garment 110 around the body 10. The at least one lace 135 may be configured to pull one portion of the garment 110 towards another portion of the garment 110 to tighten the garment 110 around a portion of the body 10. For example, the at least one lace 135 may zigzag back and forth across a length of the portion of the body 10, e.g., the inseam of a leg. In some embodiments, the at least one lace 135 may be positioned on an anterior portion of a person's body (e.g., the top or anterior portion of the leg) so as not to interfere with a person sitting in a chair or be uncomfortable on a supine patient.

The lacing guide members 140 may be any suitable size or shape that permits the at least one lace 135 to move fluidly in the lacing guide member 140. For example, the lacing guide members 140 may be enclosed to protect the at least one lace 135 or open to allow the at least one lace 135 to be moved or removed when the at least one lace 135 is loose around the lacing guide member 140. The lacing guide members 140 may change the direction of the at least one lace 135 and allow the at least one lace 135 to move fluidly without crimping, kinking or somehow impeding the movement of the at least one lace 135. For example, the lacing system 130 may be similar to lacing systems described in U.S. Pub. App. No. 2014/0094728 entitled "Motorized Tensioning System for Medical Braces and Devices," U.S. Pub. App. No. 2013/0012856 entitled "Closure System for Braces, Protective Wear and Similar Articles," U.S. Pub. App. No. 2014/0123449 entitled "Devices and Methods for Adjusting the Fit of Footwear," and U.S. Pat. No. 8,381,362 entitled "Reel Based Closure System," which are herein incorporated by reference, and/or include one or more features described therein. For example, lacing guides, motor driven systems, lacing, etc., described therein may be used alone or in combination with other elements (e.g., compression device 125, lacing system 130, etc.) to provide a donning and doffing system, and/or a compression system 100 as described herein.

The compression system 100 may also include a tightening apparatus 120 that is configured to tighten the garment 110 about the portion of the body 10. The tightening apparatus 120 may include a variety of features for use in tightening the garment 110 about the portion of the body 10. For example, the tightening apparatus 120 may include a motor driven device, a lace tension device, a motor torque or crank friction before slippage device, a drill like torque device or a fishing reel like drag device, etc.

The tightening apparatus 120 may include a tightening device 122 that may be coupled to the at least one lace 135 and configured to apply tension on the at least one lace 135 to tighten the garment 110 about the portion of the body 10. For example, the tightening device 122 may move at least a portion of the garment 110 relative to another portion of the garment 110 by tightening the at least one lace 135. In one or more embodiments, the tightening device 122 may provide pressure on one or more portions of the body 10 as the garment 110 is tightened about the portion of the body 10.

The tightening devices 122 may be operated, e.g., automatically or manually. For example, a user may push a button to activate the tightening devices 122 to tighten the at least one lace 135 or the user may manually move the tightening devices 122 to tighten the at least one lace 135. In one or more embodiments, the tightening device 122 is coupled to a first end of the at least one lace 135 and the second end of the lace is fixedly coupled (e.g., locked) into a position on the garment 110. The positions of the lacing guide members 140, through which the at least one lace 135 travels, may assist in moving (e.g., distribute) the one portion of the garment 110 relative to the other portion of the garment 110 using the tightening device 122. In some embodiments, the tightening device 122 may be described as a donning tightening device because the tightening device 122 may be configured to tighten and loosen the garment 110 about a portion of the body 10 to assist in donning and doffing the garment 110. For example, one or more embodiments, a compression garment 110 may be loosely provided about the portion of the body 10 (e.g., using one or more closures such as hook and loop closures) and thereafter, the lacing system 130 may be used to further tighten the compression garment 110 about the body portion.

Figure 11A:
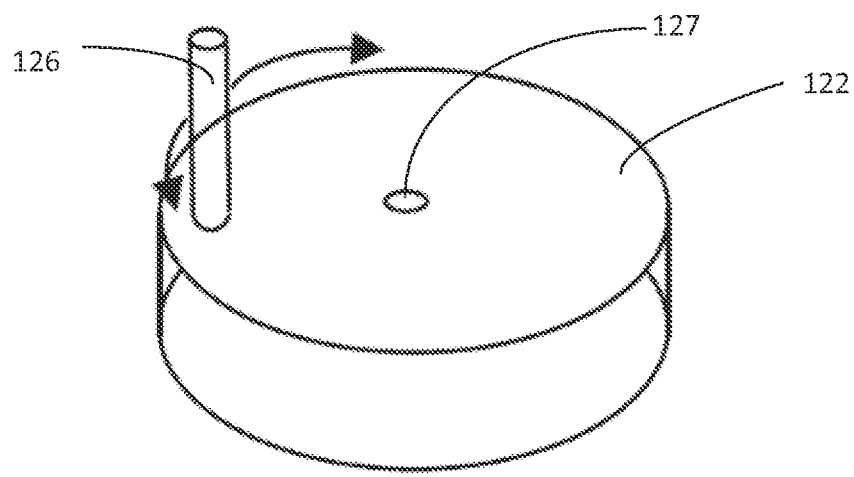
FIG. 11A is an exemplary tightening device including a knob to rotate an exemplary tightening device around a center axis that may be used with one of the exemplary compression systems shown in FIGS. 1-3.
Figure 11B:
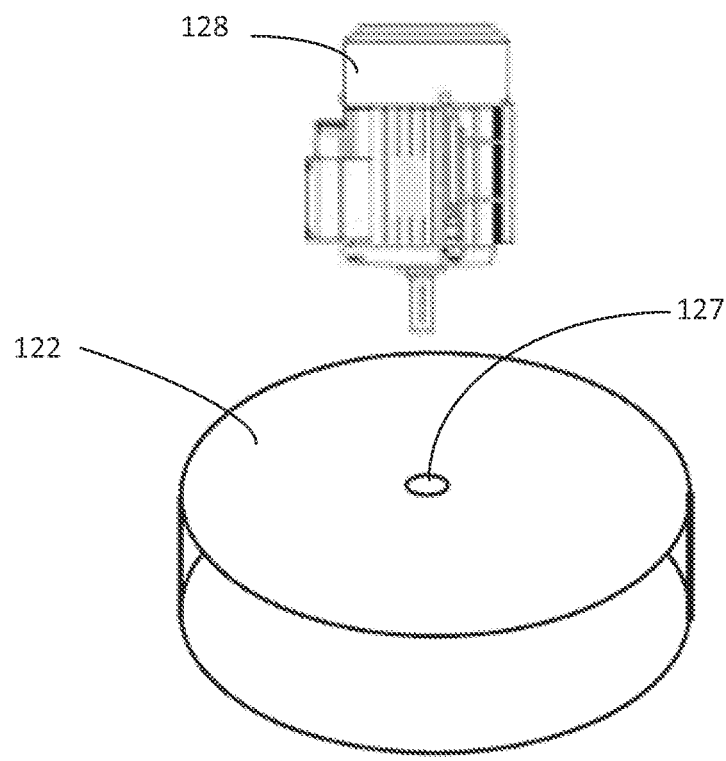
FIG. 11B is an exemplary tightening device including a motor to rotate an exemplary tightening device around a center axis that may be used with one of the exemplary compression systems shown in FIGS. 1-3.

The tightening devices 122 may include any structure suitable to provide the tightening function described herein. For example, as shown in FIGS. 11A and 11B, the tightening device 122 may include a hub or spool device that rotates around a central axis 127 and may gather the at least one lace 135 around the hub or spool. In one or more embodiments, the hub or spool of the tightening device 122 may be about the size of a single doorknob to allow the tightening device 122 to be more easily rotated by a user. In one or more embodiments, the hub or spool of the tightening device 122 may have a diameter of about, e.g., greater than or equal to 0.5 inches, greater than or equal to 1 inch, greater than or equal to 2 inches, greater than or equal to 3 inches, etc. and/or less than or equal to 6 inches, less than or equal to 5 inches, less than or equal to 4 inches, less than or equal to 2.5 inches, etc.

In one or more embodiments, the hub or spool of the tightening device 122 may be configured to handle an increased amount of lacing, for example, lacing sufficient to allow a person to don a full leg compression sleeve and then uptake a sufficient amount of the lacing to tighten the compression sleeve about the leg. In one or more embodiments, the hub or spool of the tightening device 122 may include a crank 126 (e.g., a handle), as shown in FIG. 11A, to provide easier tightening and loosening of the tightening device 122. In other embodiments, the hub or spool of the tightening device 122 may be driven by an electric motor 128, as shown in FIG. 11B, to provide easier tightening and loosening of the tightening device 122. The motor 128 may control multiple tightening devices 122 or each tightening device 122 may have its own independently controllable motor 128. In some embodiments, a rechargeable battery may power the motor 128 to provide greater patient-mobility with the compression garment 110. In one or more embodiments, the tightening device 122 may be described as being similar to the technology used for computer "mice" where the take-up spool allows the at least one lace 135 to wind or unwind as necessary. In one or more embodiments, a tool including, for example, a motor or any other apparatus allowing the user to rotate a portion of the tightening device 122 may be fixed or attached to, e.g., the garment 110 or the tightening device 122, or such tool may be removable. In other words, the tool may be removable from the tightening device 122, e.g., a removable tool that may be used to tighten or loosen each of multiple tightening devices 122. For example, the removable tool may include a motor 128 that may engage a first tightening device 122 to tighten or loosen the first tightening device 122. Thereafter, the removable tool may disengage from the first tightening device 122 and may move to and engage a second tightening device 122 to tighten or loosen the second tightening device 122. As such, the same removable tool may be used to manipulate each of a plurality of tightening devices 122.

Further, at least in one or more embodiments, the tightening device 122 may include one or more locking/unlocking features. For example, such locking/unlocking features may include actuatable unlocking structure that upon actuation allow a user to tighten the compression garment about a body portion and may include actuatable locking structure such that after the compression garment is tightened about the body portion the tightened state may be maintained (e.g., locked). Such locking and/or unlocking features may be automatic and/or manually operated. For example, such locking/unlocking functionality may be provided by structure clamping on a lace within the tightening device 122. However, any suitable structure for providing such functionality may be used.

As shown in FIGS. 1-3, the tightening apparatus 120 may also include one or more compression devices 125. The one or more compression devices 125 may be configured to control application of pressure by the plurality of pressure applying regions 114. As discussed herein, the compression devices 125 may be configured to apply pressure in a variety of ways. For example, the compression devices 125 may be configured to apply pressure through air chambers or cells, pneumatic pressure applying regions, actuatable elements applying pressure to regions, hydraulic pressure applying regions, etc. (e.g., through compartments 115 of the garment 110, through further tightening of the tightening devices 122 after the garment has been donned using a lacing system). In one or more embodiments, the one or more compression devices 125 may correspond to or include the compartments 115 of the garment 110. For example, one or more embodiments, a compression device 125 may be configured to apply pressure to a portion of the body 10 using the compartments 115 (e.g., cells) through the control of a fluid provided thereto, e.g., fluid flow, air flow, etc. In one or more embodiments, the one or more compression devices 125 may be one or more of lacing systems 130 using one or more tightening devices 122. In other words, at least in one or more embodiments, the tightening devices 122 may be used to control pressure applied to the body portion at the plurality of pressure applying regions 114 of the garment 110. In one or more embodiments, the compression devices 125 may be described as a secondary pressure applying apparatus. In one or more embodiments, the tightening device 122 and the compression device 125 may be used in combination to provide various degrees of tightening the garment 110 about the body 10 at various times, e.g., as a coarse and fine adjustment to apply pressure.

The compression system 100 may also include a controller 150 or control apparatus configured to control the pressure applied to the portion of the body 10 by each of the pressure applying regions 114 of the garment 110. For example, the controller 150 may control the pressure applied to the portion of the body 10 by each of the pressure applying regions 114 of the garment 110 through the tightening devices 122 and the compression devices 125 (e.g., controller 150 may be programmed to command the tightening devices 122 to provide pressure at the plurality of pressure applying regions 114 of the garment 110 in a particular therapy sequence such as from the distal portion of the limb to the proximate portion of the limb, may be programmed to command the tightening devices 122 to provide static and/or dynamic pressure along the body portion, etc.). In one or more embodiments, the controller 150 may be configured to control the pressure applying regions 114 independent from one another or at the same time. Further, for example, the pressure applying regions 114 may be controlled in groups or combinations. In one or more embodiments, the controller 150 may be configured to control the pressure applying regions 114 in a variety of different sequences (e.g., applying pressure in a predetermined manner) that may be, e.g., suitable for carrying out lymphedema therapy. Further, the controller 150 may control the pressure based on one or more pressures measured by one or more pressure sensors associated with the garment 110 (e.g., sensors provided in the garment 110 proximate the pressure applying regions 114).

In one or more embodiments, a control apparatus or controller 150 (e.g., one or more processors employing one or more programs or routines carrying out one or more methods or processes and implemented with one or more types of memory) may be configured to control the system and/or one or more elements thereof (e.g., tightening the garment, providing compression therapy by the one or more pressure applying regions 114, etc.). In one or more embodiments, the control apparatus may be configured to control the compression system using wired and/or wireless technology The methods and/or logic and/or configurations described in this disclosure, including those attributed to the systems, or various constituent components, may be implemented, at least in part, in hardware, software, firmware, or any combination thereof. For example, various aspects of the techniques may be implemented within one or more processors, including one or more microprocessors, microcontrollers, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices (e.g., within the system, outside of the system, or a combination of both) to support the various operations and functions described in this disclosure. In addition, any of the described components may be implemented together or separately as discrete but interoperable logic devices. Description of different features is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The controller 150 may include a tightening controller 152 configured to control the tightening devices 122 and a compression controller 154 configured to control the pressure applied to the pressure applying regions 114. In other words, the controller 150 may be configured to control the tightening devices 122 separately from controlling the compression devices 125 (e.g., separate programs may be used to separately control the various features described herein). For example, the tightening devices 122 may be independently controlled under one or more program routines for use when donning the compression garment, the tightening devices 122 may be independently controlled under one or more program routines when the tightening devices 122 are used to provide compression therapy, the plurality of pressure applying regions 114 may be controlled independently under one or more program routines when such pressure applying regions 114 of the garment are used to provide compression therapy (e.g., using a pump 102 to inflate one or more inflatable cells), the plurality of pressure applying regions 114 may be controlled independently under one or more program routines when such pressure applying regions 114 of the garment are used to provide compression therapy (e.g., using one or more electrically actuatable pressure applying regions 114), etc.

Further, the compression system 100 may include a pump 102 that may be controlled by the controller 150 (e.g., compression controller 154) to provide a fluid to/from the one or more compartments 115 of each of the pressure applying regions 114, e.g., a fluid such as a liquid or gas in the compartments 115, so as to apply a compression therapy when the compression garment 110 includes one or more fluid filled compartments 115. For example, the pump 102 may be connected to one or more of the plurality of compartments corresponding to the plurality of pressure applying regions 114 by a plurality of lines or tubing 155 so as to provide flow of fluid thereto or removal of fluid therefrom. Further, in one or more embodiments, as shown in FIG. 1, the controller 150 may be connected to one or more components of the compression garment system via one or more electrical lines and/or wirelessly, as represented generally by dashed lines 153. For example, controller 150 may be connected to communicate and control tightening devices 122 either with use of physical electrical connections and/or wirelessly.

As shown in FIG. 1, the compression system 100 may include one tightening device 122 positioned proximate the trunk of the body 10 (e.g., in a region accessible by the person wearing the garment; when tightening is performed manually). The one tightening device 122 may be coupled to at least one lace 135 that may be laced from the trunk of the body 10 to the foot of the body 10 using multiple lacing guide members 140. The one tightening device 122 may be configured to apply tension on the at least one lace 135 to, e.g., assist in donning and doffing of the garment 110.

As shown in FIG. 2, the compression system 100 may include multiple tightening devices 122 positioned along the garment 110. For example, the tightening devices 122 may be positioned proximate the trunk of the body 10 and proximate the upper leg of the body 10 (e.g., in a region accessible by the person wearing the garment; when tightening is performed manually). The tightening devices 122 may be positioned closer to the trunk of the body 10 than the foot to allow the wearer to better access the tightening device 122 with a hand (e.g., to keep the tightening devices within reach if tightening is performed manually). For example, one of the tightening devices 123 on the leg may be configured such that the at least one lace 135 coupled to the tightening device 123 may travel a distance to the lacing guide member 140 (e.g., have an extension portion 137; a relatively longer portion of lace than normal from the tightening device 123 to a first lacing guide) such that the at least one lace 135 may service a region closer to the foot but be connected to a tightening device 122 proximate the trunk of the body 10.

As shown in FIG. 3, the compression system 100 may include a tightening device 129 that may be movable along the garment 110. The tightening device 129 may be removably couplable to the garment 110 in any suitable way and to any portion of the garment 110 (e.g., trunk, thigh, knee, etc.). For example, the tightening device 129 may be removably couplable to the garment 110 by fastener, hook and loop fastener, adhesive, etc. The tightening device 129 may be movable such that the at least one lace 135 may remain coupled to the tightening device 129 when re-positioned. In one or more embodiments, the tightening device 129 may be re-positioned to help better position the tightening device 129 for user interaction. In one or more embodiments, the tightening device 129 may be re-positioned to apply additional tension on the at least one lace 135. For example, the tightening device 129 may apply tension (e.g., by rolling up the at least one lace 135) to tighten the garment 110 and then the tightening device 129 may be physically re-positioned (e.g., towards the trunk as shown by the dashed lines in FIG. 3) to provide further tension on the at least one lace 135 to further tighten the garment 110. Alternatively, the tightening device 129 may be physically re-positioned to provide tension on the at least one lace 135 and then the tightening device 129 may apply tension (e.g., by rolling up the at least one lace 135) to further tighten the garment 110.

Figure 4:
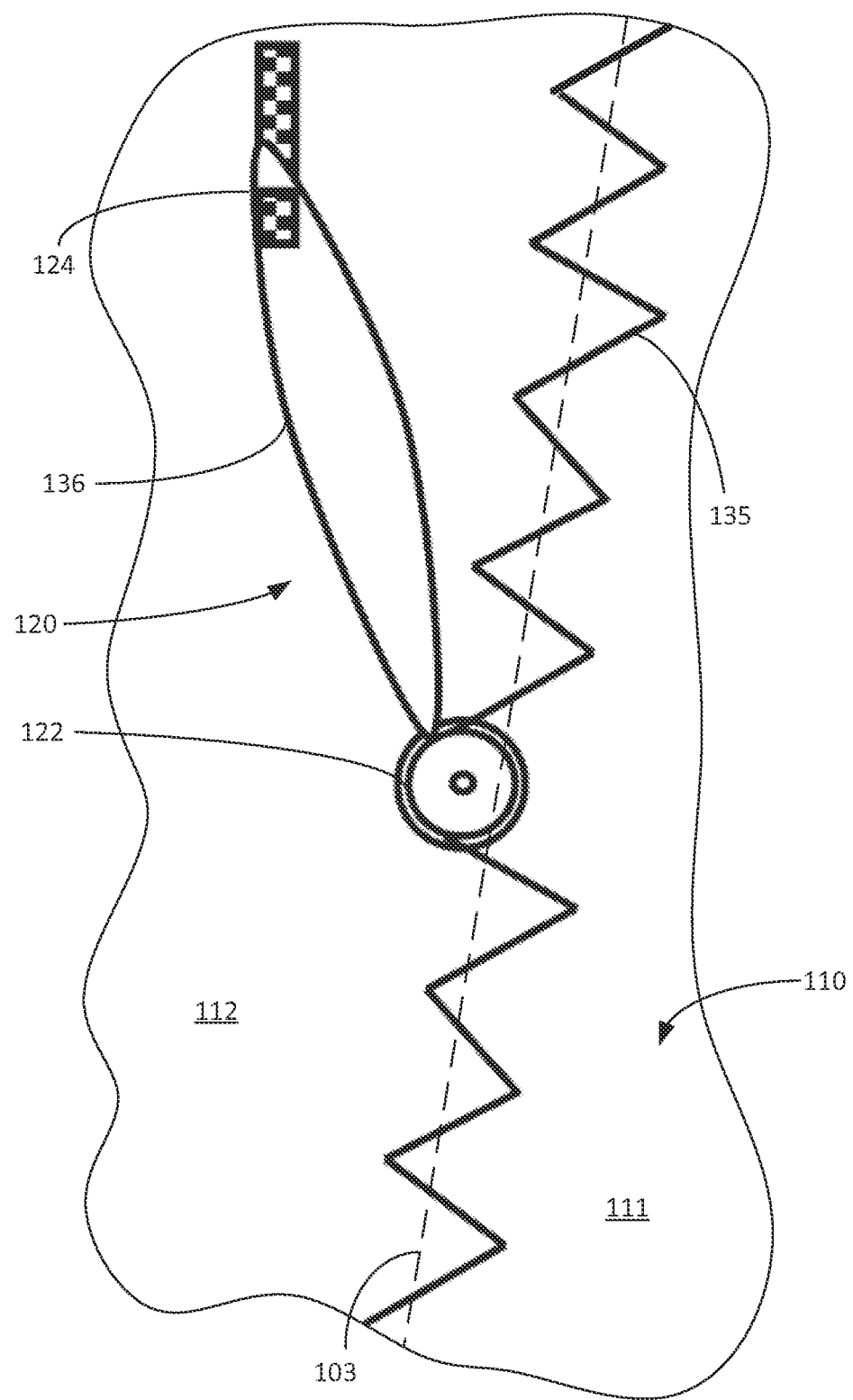
FIG. 4 is an enlarged view of an exemplary garment including a tightening apparatus and at least one lace that may be used with one of the exemplary compression systems shown in FIGS. 1-3.

One exemplary embodiment of a tightening apparatus 120 including additional tightening adjustment is shown in FIG. 4 and may be used with one or more compression systems such as the exemplary compression systems shown in FIGS. 1-3. For example, the tightening apparatus 120 may include a tightening device 122 and an additional or secondary tightening device 124. In one or more embodiments, the secondary tightening device 124 may be described as a strap device, e.g., ratcheting strap, a pull and attach strap, etc. The tightening device 122 and the secondary tightening device 124 may operate together to put multiple sources of tension on the at least one lace 135 (e.g., a course adjustment and a fine adjustment). For example, the at least one lace 135 may be guided between a first portion 111 of the garment 110 and a second portion 112 of the garment 110 by, e.g., lace guide members (not shown in FIG. 4) to move the first portion 111 relative to the second portion 112 when tension is placed on the at least one lace 135 (e.g., by the tightening device 122 or by the secondary tightening device 124). In other words, the at least one lace 135 may traverse a seam 103 between the first and second portions 111, 112 of the garment 110 to tighten the garment 110 about the body 10 (not shown in FIG. 4).

For example, in one or more embodiments, the tightening device 122 may place tension on the at least one lace 135 and then extra lace 136 of the at least one lace 135 may be positioned on the secondary tightening device 124. In other words, the tightening device 122 may provide an initial tensioning (e.g., a gross or coarse adjustment) of the at least one lace 135 and the secondary tightening device 124 may provide subsequent tensioning (e.g., a fine or final or re-dined adjustment) of the at least one lace 135 through the extra lace 136, such as by the secondary tightening device 124 ratcheting the extra lace 136 or strap in a fine adjustment procedure.

Alternatively, the extra lace 136 of the at least one lace 135 may be pulled by a user in a gross adjustment and positioned on the secondary tightening device 124 (e.g., the secondary tightening device 124 holding the extra lace 136 or strap at a fixed position) and then the tightening device 122 may place additional tension on the at least one lace 135 in a fine adjustment procedure. In other words, the secondary tightening device 124 may provide an initial tensioning (e.g., a gross or coarse adjustment) of the at least one lace 135 through pulling and attaching the extra lace 136 and the tightening device 122 may provide subsequent tensioning (e.g., a fine or final or re-fined adjustment) of the at least one lace 135.

The extra lace 136 may be positioned anywhere on the secondary tightening device 124 using, e.g., a hook, hook and loop fasteners, adhesive, clips, buttons, fasteners, etc. For example, a loop formed from the extra lace 136 may be placed on one of a plurality of hooks. Placing the extra lace 136 at different locations along the secondary tightening device 124 may provide a variety of tightening adjustments depending on the location. In one or more embodiments, the secondary tightening device 124 (e.g., a plurality of hooks) may be located, e.g., on the garment 110, off the garment 110. The secondary tightening device 124 may allow for the handling of a large amount of extra lacing 136 that otherwise may necessitate a larger tightening device 122 hub to store the extra lacing 136.

Figure 5:
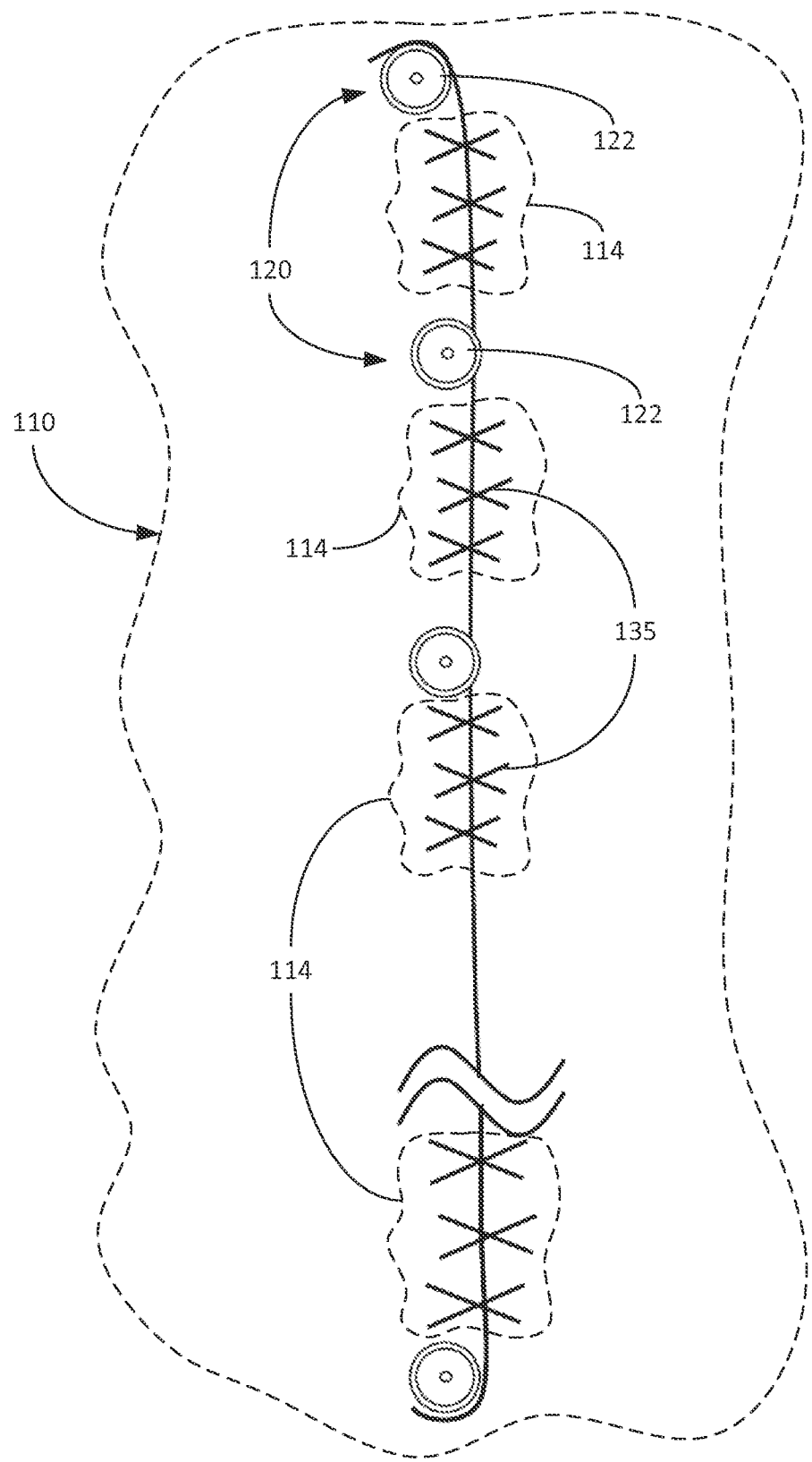
FIG. 5 is an exemplary garment including a plurality of tightening devices that may be used with one of the exemplary compression systems shown in FIGS. 1-3.

Another exemplary tightening apparatus 120 including a plurality of tightening devices 122 coupled to at least one lace 135 and located on a garment 110 is shown in FIG. 5 and may be used with one or more compression systems such as the exemplary compression systems shown in FIGS. 1-3. The tightening devices 122 may be configured to operate in a controlled manner relative to each other. For example, the tightening devices 122 may be configured to tighten the at least one lace 135 simultaneously or independent from one another. Specifically, each tightening device 122 may be configured to tighten the at least one lace 135 to an independent torque before, e.g., stopping the tightening of the at least one lace 135 associated with that particular tightening device 122, reaching a torque limit of the tightening device 122, etc.

In one or more embodiments, the tightening devices 122 may be configured to tighten the at least one lace 135 in a sequential order (e.g., in a timing chain/sequence). For example, a first tightening device 122 (e.g., associated with a pressure applying region 114) may tighten at least a portion of the at least one lace 135 (e.g., associated with a pressure applying region 114) to a certain point (e.g., for a duration of time, to an independent torque limit) and then a second tightening device 122 (e.g., associated with another pressure applying region 114) may tighten at least another portion the at least one lace 135 (e.g., associated with another pressure applying region 114) to another point. In other words, the tightening devices 122 may be controllable (e.g., by a controller) to apply pressure to the region of the body corresponding to the plurality of pressure applying regions 114 (e.g., the plurality of regions of the garment) in succession (e.g., pressure may be applied in all the pressure applying regions 114 in succession and then pressure held for a period of time, prior to release of such pressure; pressure may be applied in one or more pressure applying regions 114 and then released prior to applying pressure using one or more other pressure applying regions in a manner going from a distal body portion to a more proximal body portion; etc.). The tightening device 122 sequence may be a preprogrammed sequence or a user may be able to input a sequence.

In one or more embodiments, the controller 150, the tightening device 122 or anything driving the tightening device 122 (e.g., a motor) may be configured to control the tightening devices 122 to operate in any suitable way to, e.g., tighten the garment 110 about the portion of the body. For example, the controller 150, the tightening device 122, or anything driving the tightening device 122 (e.g., a motor) may be configured to tighten the at least one lace 135 to a prescribed pressure of the garment or a prescribed torque (e.g., a torque limit) of the tightening device 122. In one or more embodiments, the tightening devices 122 may be configured to tighten to a prescribed pressure (or torque) before stopping.

In one or more embodiments, each of the tightening devices 122 may be configured to tighten the at least one lace 135 to apply pressure to the garment at a corresponding pressure applying region 114. In other words, each tightening device 122 may correspond to a pressure applying region 114 for which the tightening device 122 tightens the garment 110. Therefore, the independent adjustment of tightening devices 122 may allow for the compression system 100 to control the sequence and degree to which pressure may be applied at each of the pressure applying regions 114. In one or more embodiments, the sequence may be determined based on a preferred order of pressure applying regions 114 to, e.g., secure fit of the garment 110 or to ensure a particular pressure applying region 114 is tighter for medical purposes (e.g., compression is provided in such pressure applying region 114). For example, on a leg compression garment a pressure applying region 114 right below the knee may be tightened first to help improve the overall fit. In another embodiment, a garment 110 may be tightened starting at a distal foot and moving proximally up a leg.

An exemplary garment 110 including a plurality of compartments 115 is shown in FIG. 6 and may be used with one or more compression systems such as the exemplary compression systems shown in FIGS. 1-3. In one or more embodiments, the plurality of compartments 115 may be described herein as compression device portions because, e.g., each of the plurality of compartments 115 may apply pressure to a portion of a body using, e.g., fluid chambers or cells, pneumatic pressure applying regions, actuatable elements applying pressure to regions, hydraulic pressure applying regions, etc. For example, with the garment 110 positioned on a body, each of the plurality of compartments 115 may be controlled to apply pressure to a portion of the body corresponding thereto (e.g., air may be supplied to inflate a compartment such that the compartment applies a pressure to a portion of the body; an electrical signal may be used to actuate an element within the garment, such as electrically actuatable fibers in the garment, such that the compartment including such fibers applies a pressure to a portion of the body; a tensioning device associated with a compartment associated with a pressure applying region may be actuated to tighten the garment relative to a portion of the body to apply a pressure thereto; etc.).

In one or more embodiments, such as those fluid filled chambers or cells to apply pressure to body portions, as well as any other embodiments requiring separation between compartments, each of the plurality of compartments 115 may be separated by welds 104. In one or more embodiments (e.g., as shown in FIG. 6), the plurality of compartments 115 may run parallel to one another along the garment 110. However, such compartments may be of any size or shape and distributed in any manner across the garment 110. Exemplary embodiments of the plurality of compartments 115 are described further herein with respect to FIGS. 8A-8C.

The tightening devices 122 and the lacing guide members 140 may be located along the edges of the garment 110 or proximate to the edges of the garment 110 as shown in FIG. 6. The at least one lace 135 may be configured to move the edges of the garment 110 relative to each other to tighten the garment 110 about a portion of the body. In one or more embodiments, the tightening devices 122 and/or the lacing guide members 140 may be located off of or apart from the edge of the garment 110 by one or more varied distances. For example, the tightening devices and/or the lacing guide members 140 may be located 0.25 inches, 0.5 inches, 1 inch, 2 inches, 3 inches, etc. away from either edge of the garment 110. In one or more embodiments, the garment 110 may include any suitable fastener to help place the garment 110 about the portion of the body. For example, the garment 110 may also include hook and loop fasteners along the edges of the garment 110 to removably couple the edges of the garment 110 to one another.

Figure 7:
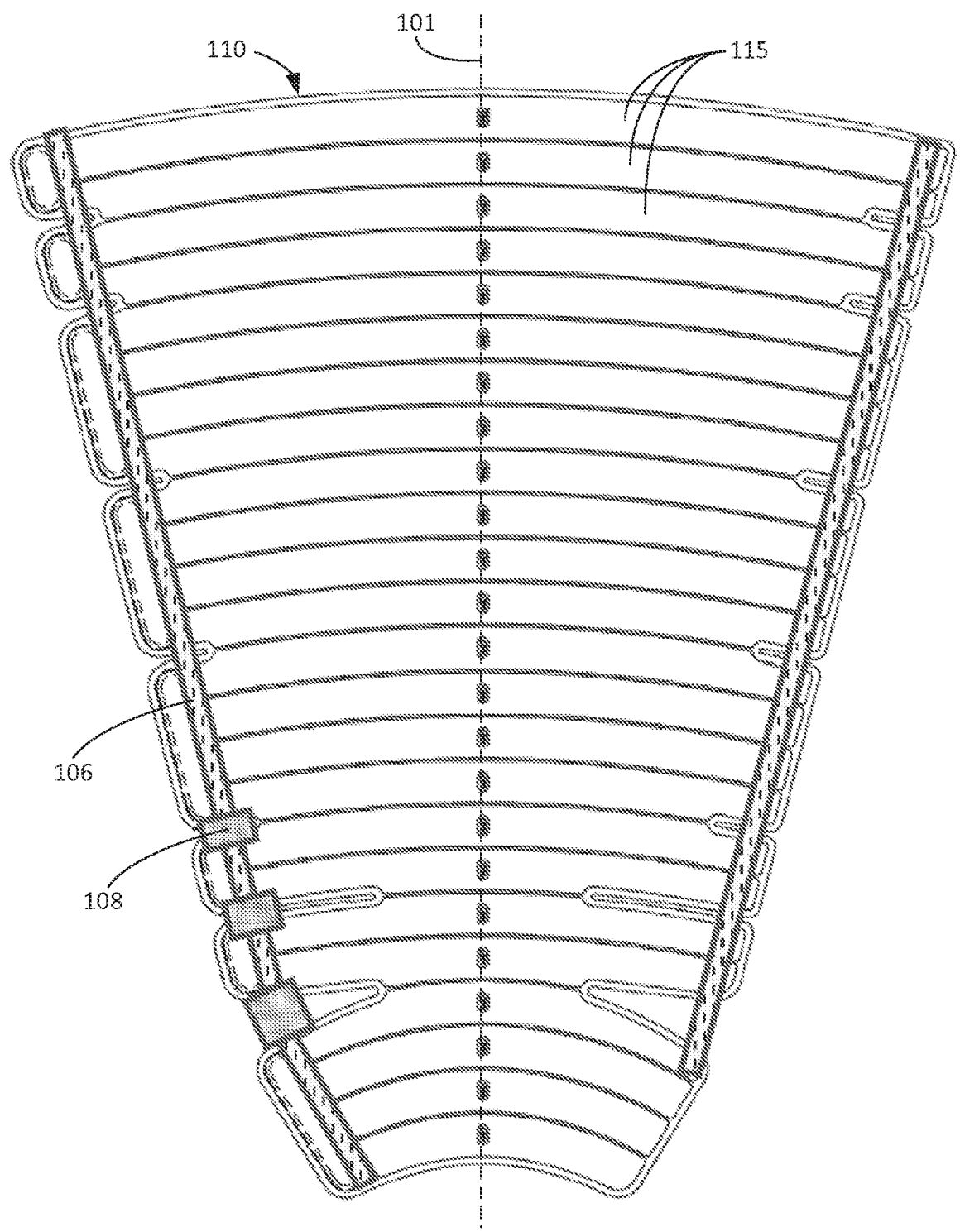
FIG. 7 is another exemplary garment including a plurality of compartments (e.g., inflatable cells) and at least one elongated rigid member that may be used with one of the exemplary compression systems shown in FIGS. 1-3.

Another exemplary garment 110 including a plurality of compartments 115 is shown in FIG. 7 and the features shown therein may be used alone, or with the tightening devices 122 and lacing guide members 140 such as shown in FIG. 6, in one or more compression systems such as the exemplary compression systems shown in FIGS. 1-3. For example, as shown in FIG. 7, the garment 110 may also include at least one elongated rigid member 106 (e.g., stays, rods, dowels, rigid elongate material, etc.) that crosses at least two adjacent compartments 115. The at least one elongated rigid member 106 may provide structural rigidity and/or stiffness to the garment 110. For example, the at least one elongated rigid member 106 may be similar to stays that are used on sailboat sails to provide sail stiffness. The at least one elongated rigid member 106 may be positioned along portions of or entirety of either edge or both edges of the garment 110. In one or more embodiments, the at least one elongated rigid member 106 may be positioned along the axis 101 of the garment. In one or more embodiments, the at least one elongated rigid member 106 may run from a foot area of the garment 110 to an upper leg area of the garment on either side of a leg compression garment. The at least one elongated rigid member 106 may be more rigid than one or more layers (e.g., see layers 116 in FIGS. 8A-8B) of the garment 110. In one or more embodiments, the at least one elongated member 106 may be used as a location to place at least one of the lacing guide members 140.

In one or more embodiments, the garment 110 may include two or more elongated rigid members 106 and at least one elastic bridge 108 that may couple two elongated rigid members 106 of the two or more elongated rigid members 106. The at least one elastic bridge 108 may provide flexibility (e.g., increase flexibility) to the rigidity of the elongated rigid members 106 to allow the garment 110 to be rigid while also flexible to conform around a portion of the body.

The garment 110 may be formed of one or more various layers 116. One or more of such layers may be coupled together while one or more other layers need not be coupled together. For example, an outer layer may not be coupled to all of the layers located more proximate to the body when the garment is worn by a user. Further, such layers may be coupled to provide compartments or may form a garment without compartments and still provide pressure applying regions 114 distributed in the garment 110 (e.g., a garment may include a plurality of electrically actuatable garment regions for applying pressure to corresponding portions of the body).

In one or more embodiments, the garment may be formed to provide the plurality of compartments. For example, the compartments 115 of the garment 110 may be provided using one or more layers 116 as shown in the cross-sections of FIGS. 8A-8C taken across, e.g., multiple compartments 115 of various exemplary garments 110. The one or more layers 116 may include, e.g., an outer layer on which the tightening apparatus may be located, one or more layers forming air cells, cushioning layers, an inelastic layer, elastic layers, etc. One or more layers 116 of the garment may include pressure sensing apparatus for sensing pressures being applied to body portions and locations corresponding to pressure applying regions 114 corresponding to compartments 115 (e.g., used to provide pressure information for controller 150 when providing compression therapy). The compartments 115 may be distributed along a length of the garment 110 or in any other manner within the garment 110. Each compartment 115 may be formed of a plurality of layers 116, with each compartment 115 separated by welds 104. In one or more embodiments, it may be described that the welds 104 couple the one or more layers 116 to define the plurality of compartments 115.

In one or more embodiments, the welds 104 may wrap around the portion of the body with the garment 110. The welds 104 may have a weld axis in the direction wrapped around the portion of the body (into the page in FIGS. 8A-8C) and a weld width perpendicular to the weld axis (e.g., the width of the weld separating the compartments). In one or more embodiments, the welds 104 may be spaced from to one another to define the multiple compartments 115. In one or more embodiments, the plurality of compartments 115 may be distributed (e.g., evenly from one another, spaced, parallel to one another, etc.) along the length of the axis of the portion of the body (e.g., axis 101 shown in FIGS. 1-3). In other embodiments, the plurality of compartments 115 may be positioned at regions or zones (e.g., the pressure applying regions 114) over the portion of the body. In one or more embodiments, each of the compartments 115 may define a pressure applying region 114.

In one or more embodiments, the compartments 115 may be configured to apply pressure to the portion of the body about which the garment 110 is, e.g., wrapped. For example, the compartments 115 may be configured to apply pressure to one or more regions (e.g., pressure applying regions 114) of the portion of the body (e.g., in a controlled manner, simultaneously, in a gradient manner, etc.). Specifically, each compartment 115 may include a compression layer 117 that may be configured to apply pressure through use of the garment 110 to a portion of the body, e.g., at the corresponding pressure applying region 114.

For example, the compression layer 117 may be configured in a variety of ways to apply pressure to a body portion corresponding to a compartment 115. Specifically, the compression layer 117 may be configured as a cell or other fluid holding region to receive a fluid (e.g., air, gas, liquid, etc.) when the compression garment is worn by a user such that expansion of the cell via, e.g., inflation, operates to apply compression to a corresponding body portion and/or may be configured to include a plurality of actuated elements (e.g., tensioned material, electrically actuatable active material, etc.) configured to apply pressure to a portion of the body. In one or more embodiments, the compression layer 117 may be described as a compression device or a secondary pressure applying apparatus. For example, in one or more embodiments, the compression layer 117 may provide a further tensioning of the garment 110 (e.g., secondary pressure applying apparatus) after a tightening apparatus tightens the garment 110 about the portion of the body. For example, the tightening apparatus may provide a gross or snug or close fit and the compression layer 117 may provide further tension or pressure (e.g., controlled pressure) to the pressure applying regions 114 (e.g., at prescribed pressures) to provide compression therapy.

Figure 8A:
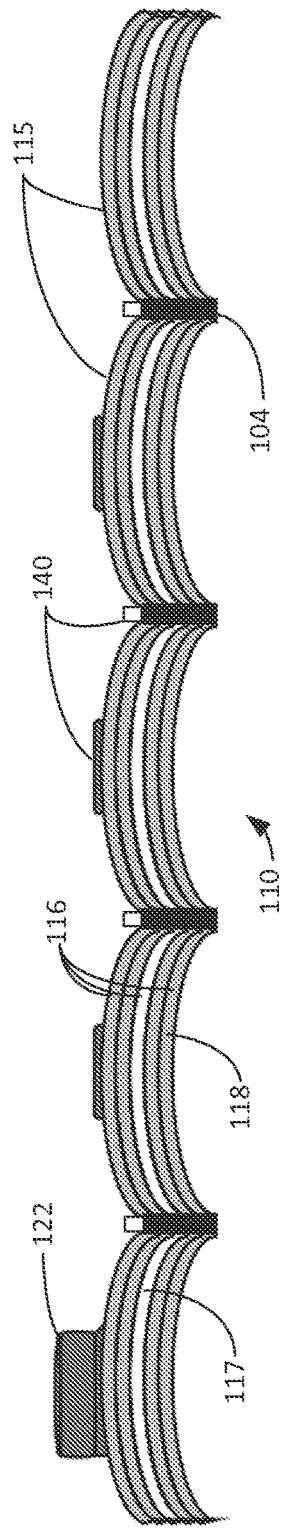
FIG. 8A is a cross-sectional view of a plurality of compartments (e.g., inflatable cells) of an exemplary garment that may be used with one of the exemplary compression systems shown in FIGS. 1-3.
Figure 8B:
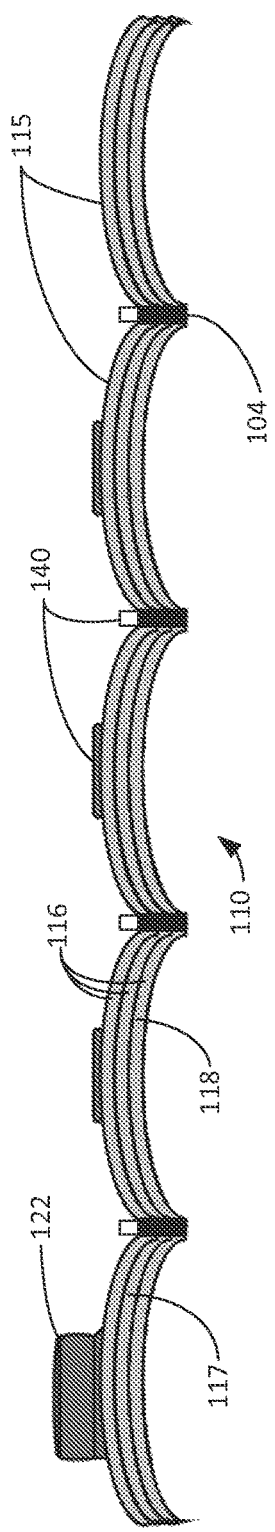
FIG. 8B is another cross-sectional view of a plurality of compartments (e.g., without inflatable cells) of an exemplary garment that may be used with one of the exemplary compression systems shown in FIGS. 1-3.
Figure 8C:
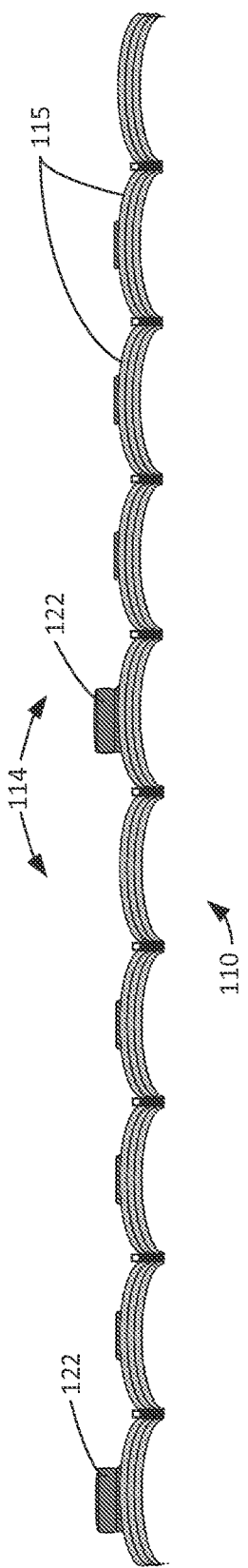
FIG. 8C is yet another cross-sectional view of a plurality of compartments of an exemplary garment (e.g., without inflatable cells) that may be used with one of the exemplary compression systems shown in FIGS. 1-3.

As shown in FIGS. 8A-8C, the tightening device 122 may be positioned on (e.g., coupled to) the garment 110 on one of the layers 116 adjacent (e.g., although not necessarily in contact with) the compression layer 117. Alternatively, the tightening device 122 may be positioned on the garment 110 on a weld 104 or at a location that does not include a compression layer 117. Additionally, the lacing guide members 140 may be positioned anywhere suitable to guide the at least one lace. For example, as shown in FIGS. 8A-8C, the lacing guide members 140 may be located within the welds 104 between the compartments 115 and/or positioned on the compartments 115. Specifically, the lacing guide members 140 may be located adjacent to and in contact with one of the welds 104 (e.g., creating a passageway through the garment 110 via the welds 104). Such lacing guide members 140 may be formed of a rigid material or flexible material. In one or more embodiments, the lacing guide members 140 may be attached to the garment 110 in any known manner. For example, such lacing guide members 140 may be welded to one or more layers 116 of the garment 110, such lacing guide members 140 may be sown to one or more layers 116 of the garment 110, the lacing guide members 140 may be attached to one of the layers 116 of the garment 110 prior to assembly of such a layer with other layers of the garment 110 (e.g., attached to a first layer and then such first layer being welded to second layer, such as in the formation of a compartment from the first and second layers), etc.

The compression system 100 may also include pressure sensor apparatus 118 configured to measure pressure applied to the portion of the body by the garment 110. The pressure sensors 118 may be located at a variety of positions along the garment 110. For example, the pressure sensors 118 may be positioned (e.g., at an equal distance apart or as necessary) along the length of the axis 101 of the garment 110. The pressure sensors 118 may be located adjacent the tightening apparatus, tightening devices 122, or one or more of the pressure applying regions 114, or multiple layers 116 of the garment 110. For example, one layer of material may encompass pressure sensing apparatus 118 comprising pressure sensing regions corresponding to the one or more pressure applying regions 114 and/or corresponding to one or more of the compartments 115. In one or more embodiments, the pressure sensor apparatus 118 may be positioned on a side of the garment 110 that may be proximate the portion of the body (e.g., opposite the tightening apparatus, opposite the tightening device 122, etc.). The pressure sensor apparatus 118 may be positioned for sensing pressure at, e.g., each pressure applying region 114, each air cell or chamber, a manifold for multiple chambers, the pressure along an entire sleeve extending along the leg, the the arm, or the like, etc. The pressure sensor apparatus 118 may be configured to measure pressure in a variety of different ways, e.g., one sensor for each pressure applying region 114, a single sensor for all of the pressure applying regions 114, etc. Additionally, the controller may be configured to control the pressure applied to the portion of the body based on the measured pressure. For example, pressure sensing apparatus may take the form of the pressure sensing described in U.S. Pat. No. 9,027,408 entitled "Elastomeric Particle Having An Electrically Conducting Surface, A Pressure Sensor Comprising Said Particles, A Method For Producing Said Sensor And A Sensor System Comprising Said Sensors," or a pump or control apparatus (e.g., 102) may be provided with pressure sensing functionality such as described in U.S. Pat. No. 7,947,003 entitled "Pressurized Medical Device," all of which are incorporated by reference herein The compression layer 117 of the garment 110 shown in FIG. 8A defines a cavity within each of the compartments 115 and which may be configured to receive fluid. The compression layer 117 of each compartment 115 may receive fluid from a source (e.g., from pump 102 shown in FIGS. 1-3) to apply pressure to body portion when garment 110 is worn by a user. For example, the fluid may be directed to each compartments 115 in a sequential or in a continuous manner from, e.g., an inlet to the garment 110 to an outlet of the garment 110. Each compartment 115 may be (e.g., individually or in groups) filled with fluid to a pressure that is to be applied to the portion of the body by the garment 110.

The compression layer 117 of the garment shown in FIG. 8B may include a variety of suitable components configured to apply pressure. For example, the pressure may be applied through the compression layer by an air or pneumatic system, a hydraulic system, an electro-mechanical system, actuated elements, a cable/lace tensioning system, or any other system that is configured to apply pressure to the portion of the body through the garment 110. Specifically, the compression layer 117 may be a plurality of actuated elements configured to apply pressure to the portion of the body (e.g., a strap tightened using a motor, actuatable material, such as nitinol, or any other compressing devices).

The garment 110 shown in FIG. 8C illustrates multiple pressure applying regions 114. For example, each pressure applying region 114 may have multiple compartments 115 configured to apply pressure to a portion of the body as well as a tightening device 122 configured to tighten at least one lace. In one or more embodiments, each pressure applying region 114 may only include one compartment 115.

A variety of lacing guide members 140 positioned with respect to welds 104 of a garment are shown in FIGS. 9-10 and may be used with one or more compression systems such as the exemplary compression systems shown in FIGS. 1-3. The lacing guide member 140 may be configured to guide the at least one lace 135 through the garment 110 such that the at least one lace 135 may assist in tightening the garment 110 about a portion of the body. Each of the lacing guide members 140 may define a lacing guide length 141 that permits the at least one lace 135 to, e.g., move fluidly in the lacing guide member 140 and/or move smoothly between lacing guide members 140.

Figure 9A:
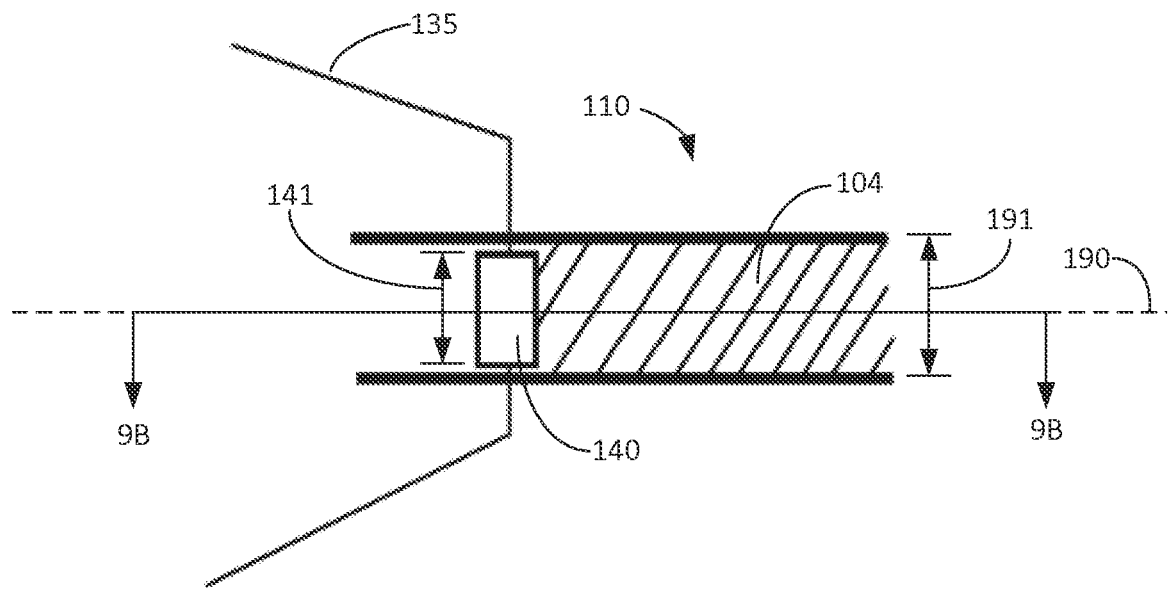
FIG. 9A is an exemplary lacing guide member located across a weld of a garment that may be used with one of the exemplary compression systems shown in FIGS. 1-3.
Figure 9B:
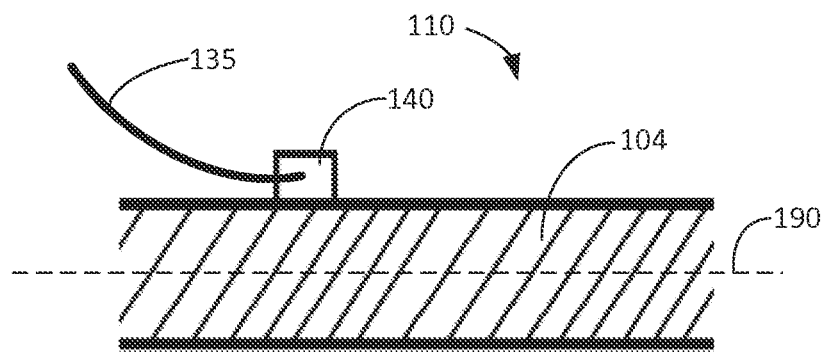
FIG. 9B is a cross-section of the weld of FIG. 9A taken across line 9B-9B that may be used with one of the exemplary compression systems shown in FIGS. 1-3.

In one or more embodiments, the lacing guide member 140 may be positioned adjacent and in contact with the weld 104. The weld 104 may extend along a weld axis 190 and define a weld width 191 perpendicular to the weld axis 190. The lacing guide member 140 may be positioned perpendicular to the weld axis 190, parallel to the weld axis 190 (e.g., between compartments 115), or at some angle to the weld axis 190. As shown in FIG. 9A, the lacing guide member 140 is positioned perpendicular to the weld axis 190 with the lacing guide length 141 of the lacing guide member 140 less than the weld width 191 of the weld 104. In other words, the lacing guide member 140 does not overlap past the weld 104. However, in some embodiments, the lacing guide member 140 may overlap past the weld 104 (e.g., the lacing guide length 141 is greater than the weld width 191) or the lacing guide length 141 may be equal to the weld width 191. As shown in FIG. 9B, the lacing guide member 140 may be positioned on the weld 104. Alternatively, the lacing guide member 140 may be positioned within the weld 104 (e.g., as shown in FIGS. 8A-8C).

The lacing guide member 140 may define a lacing guide length 141 that is greater than the weld width 191 as shown in FIG. 1.0A. The weld 104 may include an elongate weld portion 193 extending along the weld axis 190 and an additional cross weld portion 192 perpendicular to the weld axis 190. The cross weld portion 192 may be configured to provide a location for the lacing guide member 140 to be positioned on the garment. The elongate weld portion 193 may define a weld width 191 that is less than a weld length 194 of the cross weld portion 192. In other words, the weld length 194 of the cross weld portion 192 may be greater than the weld width 191 of the elongate weld portion 193. Also, the lacing guide length 141 may be less than the weld length 194 of the cross weld portion 192. In other words, the lacing guide member 140 may be contained within the cross weld portion 192. In one or more embodiments, the lacing guide length 141 may be equal to or greater than the weld length 194 of the cross weld portion 192.

Figure 10A:
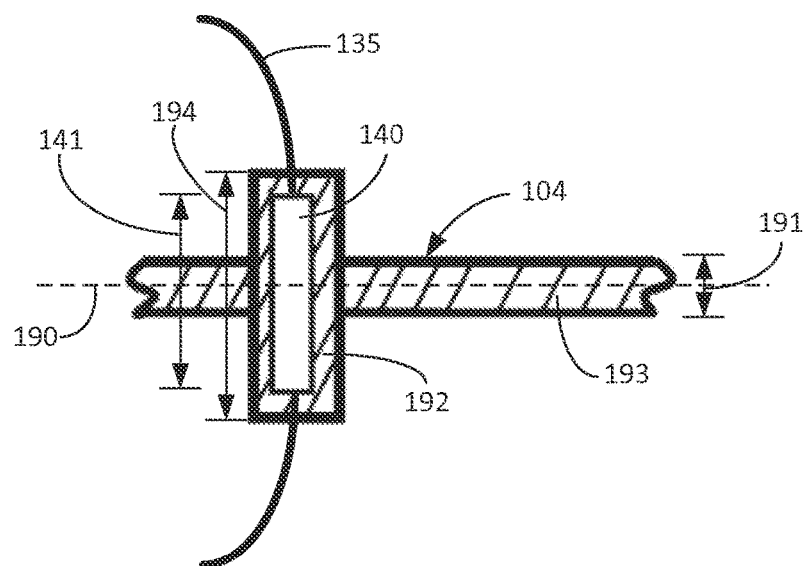
FIG. 10A is an exemplary lacing guide member located along a weld which is provided across a weld of a garment that may be used with one of the exemplary compression systems shown in FIGS. 1-3.
Figure 10B:
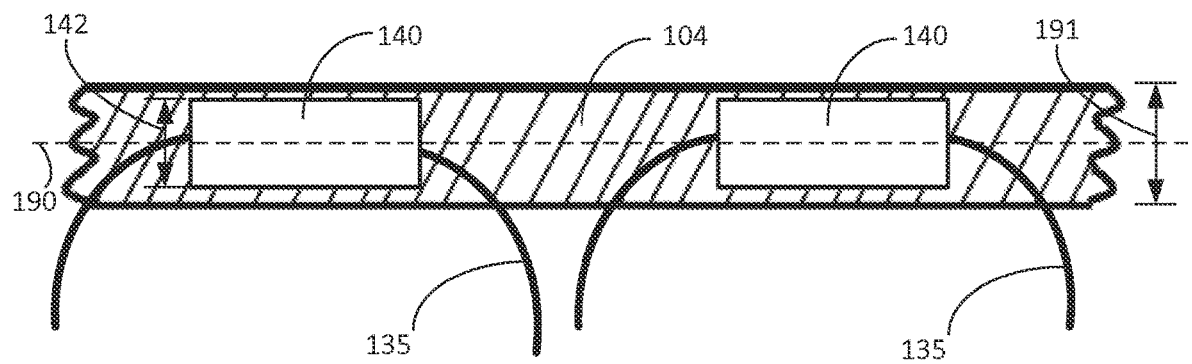
FIG. 10B is an exemplary lacing guide member located along a weld of a garment that may be used with one of the exemplary compression systems shown in FIGS. 1-3.

Further, the lacing guide member 140 may be positioned such that the lacing guide member 140 may be parallel to the weld axis 190 as shown in FIG. 10B. For example, the lacing guide member 140 may define a lacing guide width 142 that may be less than a weld width 191 of the weld 104. The at least one lace 135 may then extend along the weld 104 and be free to move along the weld axis 190 without potentially affecting the compartments of the garment. For example, the lacing guide members 140 or the at least one lace 135 may avoid the compartments of the garment when the compartments are being inflated. Additionally, the welds 104 of FIGS. 10A-10B may be larger at the location of the lacing guide member 140 than other locations of the weld 104 to, e.g., accommodate the increased size of the lacing guide member 140. In one or more embodiments, the lacing guide members 140 may be positioned as a combination of perpendicular and parallel to the weld axis 190, e.g., a combination of the lacing guide members 140 as illustrated in FIGS. 10A and 10B.

Figure 12:
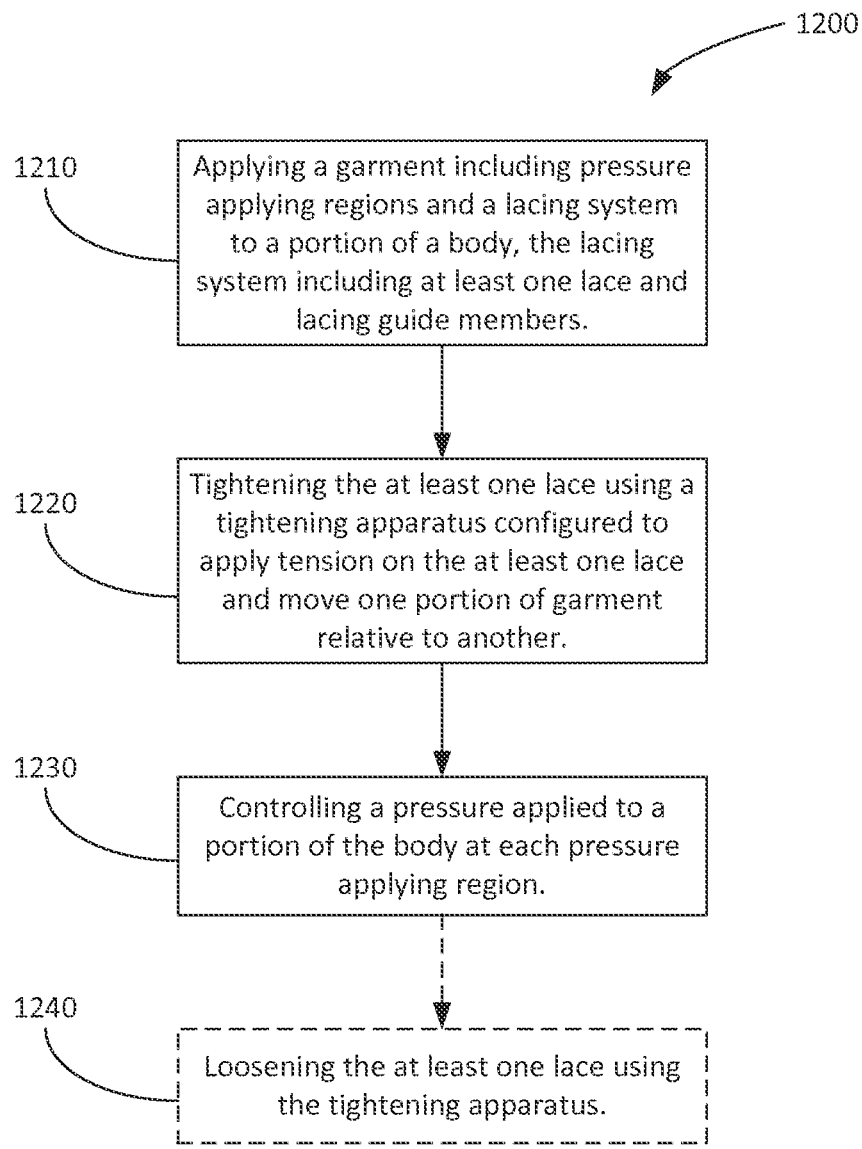
FIG. 12 is a block diagram of an exemplary method of garment compression that may be implemented using one of the exemplary compression systems shown in FIGS. 1-3.

One exemplary method 1200 of garment compression is illustrated in FIG. 12. The method may include applying 1210 a garment to at least a portion of a body (e.g., wherein the garment 110 includes a plurality of pressure applying regions 114 and a lacing system 130). The lacing system may include at least one lace that is guided by a plurality of spaced apart lacing guide members positioned on the garment. The method may also include tightening 1220 the at least one lace using a tightening apparatus (e.g., tightening device 122). The tightening apparatus may be configured to apply tension on the at least one lace and thereby move one portion of the garment relative to another (e.g., to assist in donning and doffing the garment 110). The method may further include controlling 1230 pressure applied to the portion of the body at each of the pressure applying regions (e.g., to assist in compression therapy using the garment 110 on a body and, e.g., with use of a sensor to sense the pressure being applied). In one or more embodiments, the method may further yet include loosening 1240 the at least one lace using the tightening apparatus (e.g., tightening device 122).

In one or more embodiments, the method may also include providing one or more compression devices that controllably apply the pressure to the portion of the body at each of the pressure applying regions. Each compression device of the one or more compression devices may include one or more tightening devices (e.g., tightening devices 122 controllable to tighten at least one lace 135) and/or one or more compartments (e.g., compartments 115 of the garment 110 controllable to receive fluid flow from, e.g., pump 102). In one or more embodiments, controlling 1230 pressure applied to the portion of the body at each of the pressure applying regions may include controlling each of the one or more tightening devices (e.g., tightening devices 122) operable in a lacing system (e.g. tightening device 122 coupled to at least one lace 135 and controllable to apply tension on the at least one lace 135) to apply pressure to a portion of the body corresponding to a pressure applying region. In one or more embodiments, controlling 1230 pressure applied to the portion of the body at each of the pressure applying regions may include controlling fluid flow into the one or more compartments (e.g., compartments 115) of each of the one or more compression devices (e.g. compression devices 125) to apply pressure to a portion of the body corresponding to a pressure applying region.

In one or more embodiments, the tightening apparatus may include the one or more tightening devices (e.g., tightening devices 122) configured or controllable to apply tension on the at least one lace 135 to move one portion of the garment 110 relative to another (e.g., to assist in donning and doffing of the garment 110), wherein the same or different tightening devices may apply pressure to the portion of the body at each of the pressure applying regions 114 (e.g., to assist in compression therapy using the garment 110 on a body). In one or more embodiments, controlling 1230 pressure applied to the portion of the body at each of the pressure applying regions may include a first tightening device of the one or more tightening devices controllable to apply tension on the at least one lace after a second tightening device of the one or more tightening devices applies tension on at least one lace (e.g., the tightening devices 122 may operate in a sequence to apply pressure at each of the pressure applying regions 114).

Unless otherwise indicated, all numbers expressing feature sizes, amounts, and physical properties used in the specification and claims are to be understood as being modified in all instances by the term "about" Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Particular materials and dimensions thereof recited in the disclosed examples, as well as other conditions and details, should not be construed to unduly limit this disclosure. Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed:

1. A compression system comprising:
    a flexible garment configured to wrap around at least a portion of a body, the garment comprising:
        a plurality of pressure applying regions, each configured to apply pressure to the portion of the body, wherein the plurality of pressure applying regions comprises a plurality of compartments configured to receive a fluid;
    a lacing system comprising:
        a plurality of spaced apart lacing guide members, each lacing guide member positioned at a location on the garment; and
        at least one lace guided by the plurality of lacing guide members;
    a tightening apparatus coupled to the at least one lace, wherein the tightening apparatus is configured to apply tension on the at least one lace and thereby move at least one portion of the garment relative to another portion of the garment, to tighten the garment about the portion of the body; and
    a controller configured to control the pressure applied to the portion of the body by each of the pressure applying regions of the garment in a lymphedema therapy sequence to move fluids within the lymphatic system of the body by controlling fluid flow into each of the plurality of the compartments to apply pressure to a portion of the body corresponding to a pressure applying region.

2. The compression system of claim 1, wherein the plurality of pressure applying regions is configured to apply pressure and thereby move the garment closer and towards the portion of the body.

3. The compression system of claim 1, further comprising at least one pressure sensor configured to measure pressure applied to the portion of the body by the garment, wherein the controller is configured to control the pressure applied to the portion of the body based on the measured pressure.

4. The compression system of claim 1, wherein the tightening apparatus comprises at least one tightening device configured to apply tension on the at least one lace and thereby move at least one portion of the garment relative to another to tighten the garment about the portion of the body, and further wherein the tightening apparatus is configured to apply further tension on the at least one lace after the at least one tightening device tightens the garment about the portion of the body.

5. A method of compression therapy comprising:
    applying a garment to at least a portion of a body, the garment having a plurality of pressure applying regions and a lacing system comprising at least one lace that is guided by a plurality of spaced apart lacing guide members positioned on the garment;
    tightening the at least one lace using a tightening apparatus, wherein the tightening apparatus is configured to apply tension on the at least one lace and thereby move one portion of the garment relative to another; and
    controlling pressure applied to the portion of the body at each of the pressure applying regions in a lymphedema treatment sequence to move fluids within the lymphatic system of the body.

6. The method of compression therapy of claim 5, wherein the tightening apparatus comprises one or more tightening devices, wherein controlling pressure applied to the portion of the body at each of the pressure applying regions comprises controlling each of the one or more tightening devices operable in the lacing system to apply pressure to a portion of the body corresponding to a pressure applying region.

7. The method of compression therapy of claim 6, wherein controlling pressure applied to the portion of the body at each of the pressure applying regions comprises a first tightening device of the one or more tightening devices controllable to apply tension on at least one lace after a second tightening device of the one or more tightening devices applies tension on at least one lace.

8. The method of compression therapy of claim 5, wherein the method further comprises providing one or more compression devices, wherein each compression device of the one or more compression devices comprises one or more compartments, wherein controlling pressure applied to the portion of the body at each of the pressure applying regions comprises controlling fluid flow into the one or more compartments of each of the one or more compression devices to apply pressure to a portion of the body corresponding to a pressure applying region.

9. The method of compression therapy of claim 5, further comprising loosening the at least one lace using the tightening apparatus.

10. A compression system comprising:
a garment configured to wrap around at least a portion of a body;
a lacing system comprising:
a plurality of spaced apart lacing guide members, each lacing guide member positioned at a location of the garment; and
at least one lace guided by the plurality of lacing guide members;
a tightening apparatus comprising a plurality of tightening devices corresponding to a plurality of regions of the garment and coupled to the at least one lace, wherein the tightening apparatus is configured to apply tension on the at least one lace and thereby move at least one portion of the garment relative to another portion of the garment to tighten the garment about the portion of the body, the plurality of tightening devices configured to apply a controlled pressure to a region of the portion of the body corresponding to the plurality of regions of the garment; and
a controller configured to control the pressure applied to the portion of the body by each of the plurality of regions of the garment in a lymphedema treatment sequence to move fluids within the lymphatic system of the body, wherein at least two of the plurality of tightening devices are controllable by the controller to apply the controlled pressure to the region of the portion of the body corresponding to the plurality of regions of the garment in succession.

11. The compression system of claim 10, wherein at least two of the plurality of tightening devices are controllable by the controller to simultaneously apply the controlled pressure to the region of the portion of the body corresponding to the plurality of regions of the garment.

12. The compression system of claim 10, further comprising a secondary pressure applying apparatus in addition to the tightening apparatus, wherein the secondary pressure applying apparatus is controllable by a controller to apply pressure to different regions of the portion of the body.

13. The compression system of claim 12, wherein the secondary pressure applying apparatus comprises a plurality of compartments configured to receive a fluid.

14. The compression system of claim 12, wherein the secondary pressure applying apparatus comprises a plurality of actuated elements configured to apply pressure to the portion of the body.

15. A compression system comprising:
a garment configured to wrap around at least a portion of a body, the garment comprising:
a plurality of compartments distributed along a length of the garment configured to receive a fluid, the plurality of compartments formed of one or more layers;
a plurality of welds used to couple the one or more layers to define the plurality of compartments;
two or more elongated rigid members, wherein at least one of the two or more elongated rigid members crosses at least two adjacent compartments and is more rigid than the one or more layers; and
at least one elastic bridge coupling two elongated rigid members of the two or more elongated rigid members;
a lacing system comprising:
a plurality of spaced apart lacing guide members, each lacing guide member located adjacent one of the plurality of welds; and
at least one lace guided by the plurality of lacing guide members; and
a tightening apparatus coupled to the at least one lace, wherein the tightening apparatus is configured to apply tension on the at least one lace and thereby move at least one portion of the garment relative to another portion of the garment.

16. The compression system of claim 15, wherein each of the lacing guide members comprises a guide member length that permits the at least one lace to move fluidly in the lacing guide member.

17. The compression system of claim 16, wherein at least one weld of the plurality of welds extends along a weld axis, the at least one weld comprising a weld width along the weld axis, wherein the guide member length of at least one lacing guide member is less than the weld width of the at least one weld.

18. The compression system of claim 16, wherein at least one weld of the plurality of welds comprises an elongate weld portion that extends along a weld axis and a cross weld portion extending along a cross weld axis across the elongate weld portion, wherein the elongate weld portion comprises a weld width perpendicular to the weld axis, wherein the cross weld axis of the cross weld portion extending across the elongate weld portion is greater than the weld width of the at least one elongate weld portion, and further wherein the guide member length of at least one lacing guide member is less than the cross weld axis of the cross weld portion.

19. The compression system of claim 16, wherein at least one lacing guide member of the plurality of lacing guide members is positioned on material between two welds.

20. The compression system of claim 15, wherein the tightening apparatus comprises a plurality of tightening devices configured to operate in a controlled manner relative to each other.

21. The compression system of claim 20, wherein the plurality of tightening devices are configured to operate in a sequence, wherein each of the plurality of tightening devices is configured to tighten to an independent torque.

* * * * *